(12) United States Patent
Killeen et al.

(10) Patent No.: US 9,724,401 B2
(45) Date of Patent: Aug. 8, 2017

(54) PROTEIN MATRIX VACCINE COMPOSITIONS INCLUDING POLYCATIONS

(75) Inventors: Kevin P. Killeen, Needham, MA (US); Robert T. Cartee, Newton, MA (US)

(73) Assignee: MATRIVAX, INC., Monte Carlo (MC)

(*) Notice: Subject to any disclaimer, the term of this patent is extended or adjusted under 35 U.S.C. 154(b) by 76 days.

(21) Appl. No.: 14/118,552

(22) PCT Filed: May 15, 2012

(86) PCT No.: PCT/US2012/037961
§ 371 (c)(1),
(2), (4) Date: Nov. 18, 2013

(87) PCT Pub. No.: WO2012/158701
PCT Pub. Date: Nov. 22, 2012

(65) Prior Publication Data
US 2014/0086989 A1    Mar. 27, 2014

Related U.S. Application Data

(60) Provisional application No. 61/487,663, filed on May 18, 2011.

(51) Int. Cl.
| | |
|---|---|
| *A61K 9/14* | (2006.01) |
| *A61K 39/02* | (2006.01) |
| *A61K 9/50* | (2006.01) |
| *A61K 39/09* | (2006.01) |
| *A61K 39/112* | (2006.01) |
| *A61K 39/39* | (2006.01) |
| *A61K 39/07* | (2006.01) |
| *A61K 45/06* | (2006.01) |
| *A61K 39/385* | (2006.01) |
| *A61K 39/00* | (2006.01) |

(52) U.S. Cl.
CPC ........ *A61K 39/092* (2013.01); *A61K 39/0275* (2013.01); *A61K 39/07* (2013.01); *A61K 39/385* (2013.01); *A61K 39/39* (2013.01); *A61K 45/06* (2013.01); *A61K 2039/55505* (2013.01); *A61K 2039/55516* (2013.01); *A61K 2039/55555* (2013.01); *A61K 2039/6037* (2013.01); *A61K 2039/6068* (2013.01); *A61K 2039/6093* (2013.01); *A61K 2039/70* (2013.01)

(58) Field of Classification Search
CPC .......... A61K 9/00; A61K 9/16; A61K 9/2081; A61K 9/50
USPC .................. 424/9.1, 9.2, 484, 488, 489, 499
See application file for complete search history.

(56) References Cited

U.S. PATENT DOCUMENTS

| | | | |
|---|---|---|---|
| 6,458,387 B1 * | 10/2002 | Scott et al. ............... | 424/489 |
| 2008/0095803 A1 | 4/2008 | Mekalanos | |
| 2009/0104217 A1 * | 4/2009 | Fleitmann et al. ........ | 424/189.1 |
| 2010/0226987 A1 | 9/2010 | Gnaim et al. | |

FOREIGN PATENT DOCUMENTS

| | | |
|---|---|---|
| WO | WO 00/56362 A2 | 9/2000 |
| WO | WO 01/68143 A2 | 9/2001 |
| WO | WO 2005/058940 A2 | 6/2005 |
| WO | WO 2011/031893 A1 | 3/2011 |
| WO | WO 2011/036560 A2 | 3/2011 |

OTHER PUBLICATIONS

Azze, Rolando Ochoa et al., Use of Poly-L-lysine Precoating in an ELISA for the Detection of Antibodies against Serogroup C Neisseria meningitidis Capsular Polysaccharide, Biotecnologia Aplicada, 16: 173-175 (1999).
Baudner, Barbara C. et al., Protective immune responses to meningococcal C conjugate vaccine after intranasal immunization of mice with the LTK63 mutant plus chitosan or trimethyl chitosan chloride as novel delivery platform, Journal of Drug Targeting, 13(8-9): 489-498 (2005).
Fifis, Theodora et al., Size-Dependent Immunogenicity: Therapeutic and Protective Properties of Nano-Vaccines against Tumors, Journal of Immunology, 173: 3148-3154 (2004).
Huo, Zhiming et al., Induction of Protective Serum Meningococcal Bactericidal and Diphtheria-Neutralizing Antibodies and Mucosal Immunoglobulin A in Volunteers by Nasal Insufflations of the Neisseria meningitidis Serogroup C Polysaccharide-CRM197 Conjugate Vaccine Mixed with Chitosan, Infection and Immunity, 73(12): 8256-8265 (2005).
Kabanova, Anna et al., Preparation, characterization and immunogenicity of HIV-1 related high-mannose oligosaccharides-CRM197 glycoconjugates, Glycoconj J., 27: 501-513 (2010).
Machluf et al., Enhancing the Immunogenicity of Liposomal Hepatitis B Surface Antigen (HBsAG) by Controlling Its Delivery from Polymeric Microspheres, Journal of Pharmaceutical Sciences, 89(12): 1550-1557 (2000).
Wakamoto et al., Epsilon-Polylysine Microparticle Adjuvant Drives Cytokine Production to Th1 Profile, J. Vet. Med. Sci., 69(7): 717-723 (2007).

* cited by examiner

*Primary Examiner* — Rodney P Swartz

(74) *Attorney, Agent, or Firm* — Yankwich & Associates, P.C.; Leon R. Yankwich; Michael R. Wesolowski

(57) ABSTRACT

The present invention relates to immunogenic compositions containing one or more antigens of interest, one or more carrier proteins, and one or more polycations, wherein the antigen of interest is entrapped with cross-linked carrier protein matrix and one or more polycations, methods of making such vaccines, and methods of vaccine administration.

19 Claims, 5 Drawing Sheets

PROTEIN MATRIX VACCINE COMPOSITIONS INCLUDING POLYCATIONS

CROSS-REFERENCE TO RELATED APPLICATIONS

This application is a United States national stage filing under 35 U.S.C. §371 of international (PCT) application no. PCT/US2012/037961, filed May 15, 2012, and designating the US, which claims priority to U.S. Provisional patent Application No. 61/487,663, filed May 18, 2011.

FIELD OF THE INVENTION

The invention relates to immunogenic compositions, methods of making vaccines, and methods of vaccine administration. Specifically, the invention relates to protein matrix vaccines featuring an antigen of interest entrapped in a cross-linked carrier protein matrix, wherein poly-L-lysine or other polycation(s), are used in the formation of the antigen-entrapping protein matrix.

BACKGROUND OF THE INVENTION

Vaccination against bacterial infections is an important medical pursuit, representing a preventive medical intervention recommended for virtually every individual. Design of vaccines to combat bacterial infection or the pathogenesis of bacterial infection often targets bacterial proteins, such as toxin produced by a bacterium. Such is the case, for example, in vaccines against anthrax, diphtheria, and tetanus. Another vaccine approach targets the outer capsule of a bacterium, however many of the antigens comprising a bacterial pathogen's capsule layer stimulate little or no long-term immune response, which complicates their use in creating effective vaccines. Capsules make up the outer surface of many bacteria and are typically composed of polymers of organic compounds such as carbohydrates, amino acids, or alcohols. Capsules are quite diverse chemically. For polysaccharide-based capsules the sugar units can be linked together in various molecular configurations and can be further substituted with phosphate, nitrogen, sulfate, and other chemical modifications. Capsules may be a virulence factor, by inhibiting microbes from being efficiently phagocytosed and killed by host macrophages and polymorphonuclear leukocytes.

Antibodies against capsules provide a potent defense against encapsulated organisms by mediating complement fixation on the microbial surface, which can result in bacterial lysis or opsonization, uptake, and killing by phagocytic host immune cells. The most potent antibodies against microbial capsules are IgG antibodies. Capsular antigens are generally classified as T-independent antigens as they elicit immune responses that do not involve T-cell help and therefore do not elicit long-lasting immunological memory responses. However, the covalent coupling of a protein to a capsular antigen renders the capsular antigen "T-dependent", and such T-dependent antigens then elicit a helper T cell-mediated ($T_h$-dependent) IgG-based memory B-cell, or anamnestic, response.

Various methods for rendering vaccine antigens more immunogenic and ideally T-dependent have been studied. Most bacterial surface polysaccharides are immunogenic by themselves and are capable of eliciting an immune response that will recognize the naturally occurring antigen in the microbial capsule. However, when the capsular polysaccharides alone are used as vaccines, they generally do not promote long-lasting immunity, nor are they very effective in immunizing children under the age of 2. It has been demonstrated that covalently linking a polysaccharide antigen to a carrier protein can greatly increase immunogenicity of the polysaccharide and promote the desired T-dependent immune response (or immune memory) that leads to protection of the host against subsequent infections by the antigen-bearing microorganism. For example, an unconjugated pneumococcal vaccine, such as Merck's Pneumovax®, is efficacious against invasive pneumococcal disease in individuals, however it is ineffective (e.g., in infants) at eliciting immunological memory and the desired protective immunity that would elicit long-term immunity and avoid the necessity of repeated immunizations. Conjugate pneumococcal vaccines such as Pfizer's Prevnar® (Pfizer Inc., USA), have been shown to be highly immunogenic even in 2-month old infants, induce T-dependent immunity and to be highly efficacious.

However, while conjugate vaccines are promising immunologically, they can be extremely difficult and complicated (and expensive) to manufacture, greatly deterring their distribution to those in need of vaccination throughout the world. For example, in the case of Prevnar®7, each *S. pneumoniae* strain used to provide the seven polysaccharide antigens used for conjugation is grown in a bioreactor; the cells are harvested; polysaccharide is extracted, purified, hydrolyzed to the appropriate size; the individual antigens are then conjugated to a protein carrier; the conjugate is re-purified, mixed with the additional 6 other polysaccharide-protein complexes (conjugates) that were prepared in a similar manner; and the multi-conjugate mixture is finally adjuvanted with alum. It is estimated that there are more than 200 GMP steps in the manufacture of the heptavalent Prevnar® vaccine.

Recently, protein matrix vaccines have been proposed as an alternative to conjugate vaccines. See, US published application no. US-2008-0095803 (Mekalanos, J.), published Apr. 24, 2008; international patent application publication no. WO 2008/021076 (Mekalanos, J.), published Feb. 21, 2008; and international patent application publication no. WO 2011/031893 (Killeen, K., et. al.), published Mar. 17, 2011), incorporated herein by reference. Rather than covalently conjugating an antigen of interest to a carrier, a protein matrix vaccine entraps the antigen in a carrier protein matrix, prepared by cross-linking the carrier protein in the presence of the desired antigen. Significant covalent linking of the antigen to the carrier protein is avoided; rather, the antigen remains associated with the matrix by becoming entrapped by the protein carrier during matrix formation (cross-linking reaction). Such protein matrix vaccines have been demonstrated to elicit greater immunogenicity than vaccines prepared using the antigen alone; and protein matrix vaccines may also elicit the sort of immune response (i.e., induction of T-dependent immunity) seen with conjugate vaccines. Synthesis of protein matrix vaccines does not involve complicated conjugation reactions, and typically requires fewer processing steps, which makes the protein matrix vaccines, in turn, less expensive to manufacture than a conjugate vaccine.

Although protein matrix vaccines provide several advantages, the titer of antigen-specific antibodies elicited by protein matrix vaccines is often lower than the titer elicited by a corresponding conjugate vaccine. WO 2011/031893 teaches that separating the protein matrix vaccines by size exclusion chromatography and selecting the fractions containing high molecular weight protein matrix particles for immunization can lead to titers similar to those elicited by conjugated polysaccharide vaccines. However, it is a persistent technical problem in the field to provide a means for producing protein matrix vaccines of increased immunogenicity, in order to exploit the scientific promise and the manufacturing and cost advantages of this emerging technology. There is a continuing need for improved protein matrix vaccines having enhanced immunogenicity or potency.

SUMMARY OF THE INVENTION

A surprising advance in the effectiveness and yield of protein matrix vaccines has been achieved with vaccines prepared according to the present invention, in which poly-L-lysine (PLL), or another polycation, is used in the formation of the entrapping protein matrix for a polysaccharide or other antigen. Thus, the quality and yield of protein matrix vaccines have been improved not by modification of the antigen(s), but by attention to the nature and composition of the matrix used to entrap the antigen(s).

Described herein are new protein matrix vaccines and methods for improving polysaccharide entrapment with the matrix by using primary amine containing polycations.

One embodiment of the invention is an immunogenic composition comprising (1) one or more antigen of interest, (2) one or more carrier protein, and (3) one or more polycation, wherein said carrier protein and optionally said polycation are cross-linked to form a protein matrix, and said antigen of interest is entrapped by said protein matrix. Such compositions may be readily prepared by admixing the antigen, carrier protein, and polycation components, initiating a cross-linking reaction to cause cross-linking of the carrier protein and/or polycation. The protein matrix vaccine compositions incorporating a polycation, e.g., α-PLL, according to the present invention have increased immunogenicity compared to the antigen alone, compared to a mixture of antigen and carrier, and compared to a protein matrix vaccine composition not incorporating a polycation.

In a preferred embodiment, the one or more polycations of the immunogenic composition is selected from the group consisting of: poly-L-lysine, poly-L-arginine, poly-ornithine, spermidine, spermine, chitosan [a β-(1-4)-linked copolymer of 2-amino-2-deoxy-β-D-glucan (GlcN) and 2-acetamido-2-deoxy-β-D-glucan (GlcNAc)], branched polyethylenimine (PEI), Polyamine N7 (CAS 29320-38-5) and Ethylenediaminomethyl polystyrene (CAS 177987-93-8). In desirable embodiments, said polycation is poly-L-lysine (PLL).

In additional desirable embodiments said poly-L-lysine is alpha poly-L-lysine (α-PLL; αPLL) or epsilon poly-L-lysine (ε-PLL; εPLL).

In preferred embodiments, said composition is comprised of protein matrix particles having a mean particle size greater than 50 nm diameter. Such compositions may be readily prepared by admixing the antigen, carrier protein, and polycation components, initiating a cross-linking reaction to cause cross-linking of the carrier protein and/or polycation, followed by processing of the reaction products to eliminate lower molecular weight species.

One embodiment of the invention is a vaccine composition containing an antigen of interest and a carrier protein/polycation matrix, where the antigen is entrapped with the carrier protein/polycation matrix to form a complex. In desirable embodiments of the invention, the antigen/carrier protein/polycation matrix complex has a mean particle size diameter above 50 nm. In more desirable embodiments of the invention, the complex has a mean particle size diameter of greater than 100 nm, greater than 150 nm, greater than 200 nm, greater than 500 nm, greater than 1000 nm, greater than 2000 nm or even larger, e.g., to the limits of the methodology for separating the protein matrix particles. In yet more desirable embodiments of the invention, the antigen/carrier protein/polycation matrix complexes of the vaccine composition will encompass a range of particle sizes above 50 nm in diameter, such as 50-2000 nm diameter, or selections within that range, e.g., 100-200 nm, 200-400 nm, 250-500 nm, 120-1000 nm, 200-2000 nm, and other such particle size ranges. In yet further desirable embodiments of the invention, the composition includes complexes having particle sizes of 50-150 nm diameter.

In additional desirable embodiments of the invention, the molar ratio of the antigen to the carrier protein is between 1 to 10 and 10 to 1.

In preferred embodiments, the percentage of polycation by weight in the reaction mixture is 0.005 to 0.10%, or in the range of 0.05 mg/ml-0.5 mg/ml.

In additional desirable embodiments, the immunogenic composition further includes two or more antigens of interest, for example, 2, 3, 4, 5, 6, 7, 8, 9, 10, 11, 12, 13, 14, 15, 16, 17, 18, 19, 20, 21, 22, 23, or more antigens of interest.

In desirable embodiments of the invention, the protein matrix vaccine compositions of the invention, when administered to a mammal, elicit a T cell-dependent immune response in the mammal (i.e., produce immunological memory in the vaccinated host).

In desirable embodiments of the invention, said antigen of interest is a polysaccharide.

In additional desirable embodiments of the invention, the polysaccharide is selected from the group consisting of a *Streptococcus pneumoniae* polysaccharide, *Francisella tularensis* polysaccharide, *Bacillus anthracis polysaccharide, Haemophilus influenzae* polysaccharide, *Salmonella Typhi* polysaccharide, *Citrobacter freundii* polysaccharide, *Salmonella* species polysaccharide, *Shigella* polysaccharide, or *Neisseria meningitidis* polysaccharide. O-antigens of Gram negative bacteria, part of LPS (lipopolysaccharide) that is unique and often a protective antigen for bacterial infection, are also suitable antigens of interest for use in the present invention.

In further desirable embodiments of the invention, said *Streptococcus pneumoniae* polysaccharide is selected from one or more polysaccharide of the group consisting of capsular type 3, 4, 6B, 7A, 7B, 7C, 7F, 9A, 9L, 9N, 9V, 12A, 12B, 12F, 14, 15A, 15B, 15C, 15F, 17, 18B, 18C, 19F, 23F, 25A, 25F, 33F, 35, 37, 38, 44, and 46.

In preferred embodiments, the one or more carrier protein is selected from the group consisting of diphtheria toxoid, e.g., the non-toxic diphtheria toxin protein fragment CRM197, tetanus toxoid, *Pseudomonas aeruginosa* exotoxin A or a mutant thereof, cholera toxin B subunit, tetanus toxin fragment C, bacterial flagellin, pneumolysin, an outer membrane protein of *Neisseria meningitidis, Pseudomonas aeruginosa* Hcp1protein, *Escherichia coli* heat labile enterotoxin, shiga-like toxin, human LTB protein, listeriolysin O, a protein extract from whole bacterial cells, the dominant negative inhibitor (DNI) mutant of the protective antigen of *Bacillus anthracis*, or Escherichia coli beta-galactosidase.

In desirable embodiments of the invention, the immunogenic composition comprises an antigen of interest entrapped in a carrier protein/polycation matrix and further includes a pharmaceutically acceptable excipient.

In preferred embodiments, the invention features another method of making a vaccine composition. This method involves (i) mixing one or more antigens of interest, one or more carrier proteins, and one or more polycations and (ii) adding a cross-linking agent capable of forming cross-links between carrier protein molecules, between different sites of the same carrier protein molecule, and/or between the carrier protein molecule and the polycation, and (iii) initiating a cross-linking reaction. In additional embodiments, the method of making a vaccine according to the invention will also include a further step (iv) of optionally selecting from the cross-linking reaction product complexes having a particle size diameter of greater than 50 nm. In certain cases where the reactive groups of the cross-linking reagent and the reactive sites of the carrier protein will react on contact, the admixture and initiation steps (ii) and (iii) will occur simultaneously or may be considered one step. Additionally, it may be advantageous to quench the cross-linking reaction by including a step after the reaction initiation step of attenuating the cross-linking reaction, e.g., by addition of an appropriate quenching or blocking agent.

In desirable embodiments of the invention, the invention features a method of eliciting an immune response in a mammal to an antigen of interest or vaccinating a subject against an infectious agent, the method comprising administering to the mammal or subject an immunogenic composition as described herein. In preferred embodiments, the mammal is a human.

In further desirable embodiments of the invention, the invention features a vaccine composition comprising two or more immunogenic compositions described herein.

Other features and advantages of the invention will be apparent from the following detailed description, the drawings, and the claims.

DETAILED DESCRIPTION OF THE INVENTION

Figure 1:
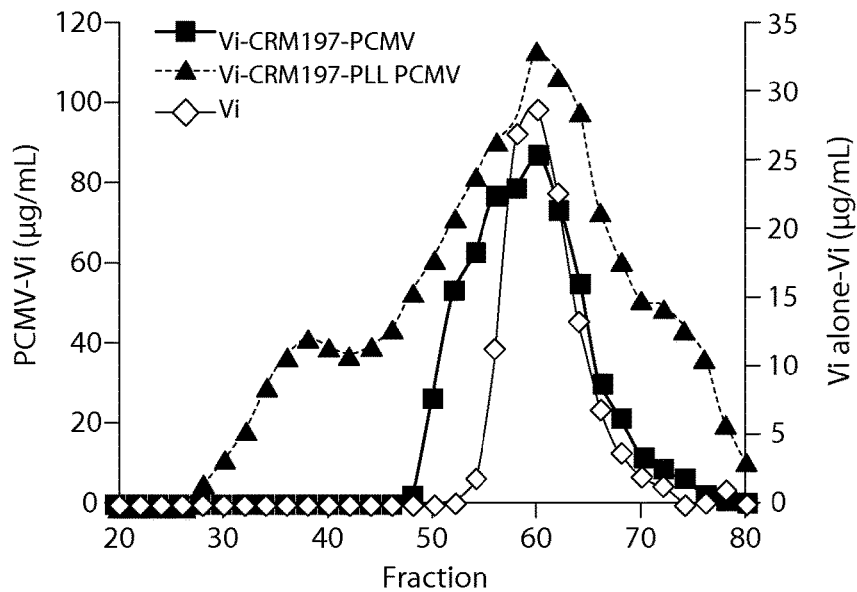
FIG. 1 is a graph showing the separation of Vi-CRM197 PCMV reactions, with and without poly-L-lysine (PLL), by size exclusion chromatography. Vi polysaccharide alone, a Vi-CRM197 PCMV reaction that contained PLL, and a Vi-CRM197-PCMV that contained no PLL were separated on a 500 mL (90 cm×2.6 cm) Sephacryl S-1000 column. The amount of Vi polysaccharide in the fractions was determined using the Stains-all assay.

Protein matrix vaccines, and particularly protein capsular matrix vaccines (PCMVs), are described in US patent publication US-2008-0095803 (Mekalanos, J.), published Apr. 24, 2008; international patent application publication no. WO 2008/021076 (Mekalanos, J.), published Feb. 21, 2008; and international patent application publication no. WO 2011/031893 (Killeen, K., et. al.), published Mar. 17, 2011, all incorporated herein in their entirety. These publications teach that protein matrix vaccines have the potent immunological properties of typical PS-protein conjugate vaccines but desirably differ from conjugate vaccines in that no significant covalent bonding occurs to couple the antigen of interest to the carrier protein. Thus, the protein matrix vaccines (carrier protein matrix/antigen complexes) are distinguished from conventional conjugate vaccines, wherein the antigen is covalently bound to a carrier. In a protein matrix vaccine, the antigen of interest, e.g., polysaccharides, capsular organic polymers or other antigen, is entrapped within a carrier protein matrix.

When a capsular biopolymer or polysaccharide of a pathogen is entrapped in a cross-linked protein matrix, such vaccines are termed protein capsular matrix vaccines (PCMVs). As described in WO 2008/021076 and US 2008-0095803, PCMVs were produced including ones based on the model T-independent capsular antigen, poly-gamma-D-glutamic acid (PGA), as well as alginic acid (alginate) and dextran, and the exemplary carrier protein, Dominant Negative Inhibitor mutant (DNI). DNI is a mutated form of Protective Antigen (PA) of *B. anthracis* and was produced from *Escherichia coli* by the method of Benson, et al., *Biochemistry*, 37:3941-3948 (1998). Other PCMV embodiments, as well as the benefits of size-fractionating the PCMV particles, are described in WO 2011/031893.

The present invention relates to discoveries and observations made in respect of enhancing the immunogenicity and yield of protein matrix vaccine compositions through improved entrapment of the antigen within the protein matrix.

In order that the invention may be more clearly understood, the following abbreviations and terms are used as defined below.

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step. It is also understood that an element or step "selected from the group consisting of" refers to one or more of the elements or steps in the list that follows, including combinations of any two or more of the listed elements or steps.

The term "administering" as used herein in conjunction with a vaccine composition, means providing the vaccine composition to a subject such as a human subject in a dose sufficient to induce an immune response in the subject, where the immune response results in the production of antibodies that specifically bind an antigen contained in the vaccine composition (i.e., which antigen, in therapeutic vaccines, corresponds to an antigenic marker on a pathogen). Administering desirably includes intramuscular injection, intradermal injection, intravenous injection, intraperitoneal injection, subcutaneous or transcutaneous injection, inhalation, or ingestion, as appropriate to the dosage form and the nature and activity of the vaccine composition to be administered. Administering may involve a single administration of a vaccine or administering a vaccine in multiple doses. Desirably, a second ("booster") administration is designed to boost production of antibodies in a subject to prevent infection by an infectious agent. The frequency and quantity of vaccine dosage depends on the specific activity of the vaccine and can be readily determined by routine experimentation.

The term "cross-link" or "crosslink" refers to the formation of a covalent bond between two molecules, macromolecules, or combination of molecules, e.g., carrier protein molecules, or between two sites of the same molecule, e.g., two amino acid residues of the same protein, or between carrier protein molecules and polycation molecules, either directly, when a "zero-length" linker is used (creating a direct bond), or by use of a bifunctional cross-linker molecule that forms a molecular bridge or link between two reactive sites. Bifunctional cross-linkers exhibit two functional groups, each capable of forming a covalent bond with one of two separate molecules or between two separate groups in the same molecule (i.e., so as to form "loops" or "folds" within a molecule such as a carrier protein). Exemplary linkers include bifunctional cross-linkers which are capable of cross-linking two carrier protein molecules and/or two polycation molecules and/or a carrier protein molecule with a polycation molecule.

The term "antigen" as used herein refers to any molecule or combination of molecules that is specifically bound by an antibody or an antibody fragment.

The term "bifunctional cross-linker" or "bifunctional linker" as used herein means a compound that has two functional groups, each separately capable of forming a covalent bond with reactive groups on two separate molecules, atoms, or collections of molecules desired to be linked together. Exemplary bifunctional linkers are described, for example, by G. T. Hermanson, *Bioconjugate Techniques* (Academic Press, 1996) and Dick and Beurret, "Glycoconjugates of Bacterial Carbohydrate Antigens," in *Conjugate Vaccines* (Cruse and Lewis, eds), *Contrib. Microbiol. Immunol. Basel, Karger*, 1989, vol. 10, pp. 48-114). Desirably a bifunctional linker is glutaraldehyde, bis[sulfosuccinimidyl]suberate, or dimethyl adipimidate.

The term "linker" or "cross-linker" as used herein refers to a compound capable of forming a covalent chemical bond or bridge that joins two or more molecules or two or more sites in the same molecule. Desirable linkers include, e.g., glutaraldehyde or other dialdehydes of the formula OHC—R—CHO, where R is a linear or branched divalent alkylene moiety of 1 to 12 carbon atoms, a linear or branched divalent heteroalkyl moiety of 1 to 12 atoms, a linear or branched divalent alkenylene moiety of 2 to 12 carbon atoms, a linear or branched divalent alkynylene moiety of 2 to 12 carbon atoms, a divalent aromatic radical of 5 to 10 carbon atoms, a cyclic system of 3 to 10 atoms, —$(CH_2CH_2O)_qCH_2CH_2$— in which q is 1 to 4, or a direct chemical bond linking two aldehyde groups. Linking may be direct without the use of a linking (bridging) molecule. For example, a carboxyl group, for instance on the side chain of an Asp or Glu residue in a carrier protein carboxyl group may be linked directly to a free amino group, for instance on the side chain of a Lys residue, using carbodiimide chemistry or enymatically using transglutamidases which catalyze cross-linking between free amino groups and carboxamide groups, e.g., of Gln residues.

The term "boost" in the context of eliciting production of antibodies refers to the activation of memory B-cells that occurs during a second exposure to an antigen. This is also referred to as a "booster response" and is indicative of a long-lived "secondary" memory immune response, resulting in the long-lived capacity to produce antibodies.

The term "carrier protein" in the context of a vaccine composition refers to a protein used in a vaccine composition that elicits an immune response to itself and/or to an antigen associated with or complexed with such carrier protein and polycation. In a protein matrix vaccine composition of the present invention, an antigen is entrapped within a matrix of carrier proteins are cross-linked to each other and/or polycations, preferably without significant covalent linkage of antigen to the matrix. In a conjugate vaccine composition, an antigen is reacted with a carrier protein, so that the antigen and carrier protein are covalently linked to each other, by design. Desirably, the carrier protein contains epitopes recognized by a T-helper cell. Also encompassed by the definition of a "carrier protein" are multiantigenic peptides (MAPs), which are branched peptides having a plurality of reactive sites. Desirably, a MAP includes lysine (Lys) residues. Exemplary desirable carrier proteins include toxins and toxoids (chemical or genetic), which may be mutated, e.g., to reduce reactogenicity. Suitable carrier proteins include, e.g., diphtheria toxin or a non-toxic mutant thereof, e.g., diphtheria toxoid, tetanus toxin or a non-toxic mutant thereof, e.g., tetanus toxoid, *Pseudomonas aeruginosa* exotoxin A or a non-toxic mutant thereof, cholera toxin B subunit, tetanus toxin fragment C, bacterial flagellin, pneumolysin, listeriolysin O (LLO, and related molecules), an outer membrane protein of *Neisseria meningitidis*, *Pseudomonas aeruginosa*Hcp1 protein, *Escherichia coli* heat labile enterotoxin, shiga-like toxin, human LTB protein, a protein extract from whole bacterial cells, the dominant negative inhibitor mutant (DNI) of the Protective Antigen of *Bacillus anthracis*, or *Escherichia coli* beta-galactosidase, or any other protein that can be cross-linked to form a matrix capable of entrapping an antigen of interest.

The term "entrapped" as used herein in reference to an antigen means association or complexing of an antigen with a carrier protein and polycation, in particular a cross-linked carrier protein optionally also cross-linked with a polycationic molecule to form a matrix which forms the association or complex with the antigen, such that antigen remains in the complex with carrier protein and polycation under physiological conditions. Desirably, the antigen is entrapped in a complex with carrier proteins and polycation in the absence of significant covalent bonding between the antigen and a carrier protein/polycation. "Absence of significant covalent bonding", as used herein, refers to no more than 50% of the antigen being covalently bound to a carrier protein. Desirably, no more than 40%, no more than 30%, no more than 20%, no more than 10%, or desirably, no more than 5% of the antigen is covalently bonded to carrier protein or polycation in a protein matrix vaccine composition. As will be appreciated from the disclosure below, the object of protein matrix vaccine design and production is to avoid the laborious chemical linking of antigen to a carrier that is the chief characteristic of conjugate vaccines. In a protein matrix vaccine the antigen is associated with the carrier by entrapment in a cross-linked matrix rather than by conjugation to the carrier, and in fact to the extent possible cross-linking of antigen to a carrier protein or carrier protein/polycation matrix is avoided. In processes for making protein matrix vaccines, the antigen is included in the admixture of matrix components intended to become cross-linked, but by design the antigen does not participate in the cross-linking reaction or at least does not participate in a significant amount of cross-linking. Carrying out the protein matrix formation in the presence of antigen, however, leads to the antigen becoming entrapped in, without significant cross-linking to, the carrier protein matrix (or carrier protein/polycation matrix in one embodiment of this invention).

By "infection" is meant the invasion of a subject by a microbe, e.g., a bacterium, fungus, parasite, or virus. The infection may include, for example, the excessive multiplication of microbes that are normally present in or on the body of a subject or multiplication of microbes that are not normally present in or on a subject. A subject is suffering from a microbial infection when an undesirably (e.g., pathogenic) excessive microbial population is present in or on the subject's body or when the presence of a microbial population(s) is damaging the cells or causing pathological symptoms in a tissue of the subject.

By "infectious agent" is meant a microbe that causes an infection.

The term "immunogenic" refers to a compound that induces an immune response in a subject. Desirably, an immune response is a T cell-dependent immune response that involves the production of IgG antibodies.

The term "microbial capsular polymer" refers to a polymer present in or on the capsule coating of a microbe. Desirably, a microbial capsular polymer is an organic polymer such as a polysaccharide, phosphopolysaccharide, polysaccharide with an amino sugar with a N-acetyl substitution, polysaccharide containing a sulfonylated sugar, another sulfate-modified sugar, or phosphate-modified sugar, polyalcohol, polyamino acid, teichoic acid, or an O side chain of a lipopolysaccharide.

"Monomer" refers to a molecular structure capable of forming two or more bonds with like monomers, often yielding a chain or a series of branched, connected chains of repeating monomer substructures, when part of a "polymer."

"Organic polymer" refers to a polymer composed of covalently linked monomers each composed of carbon, oxygen, hydrogen, or nitrogen atoms or phosphate or sulfate moieties. Desirably, an organic polymer is a polysaccharide, phosphopolysaccharide, polysaccharide with an amino sugar with a N-acetyl substitution, polysaccharide containing a sulfonylated sugar, another sulfate-modified sugar, or phosphate-modified sugar, sugar, polyalcohol, polyamino acid, teichoic acid, and an O side chain of lipopolysaccharide.

"Polyalcohol" means a hydrogenated form of a carbohydrate where a carbonyl group has been reduced to a primary or secondary hydroxyl group. Exemplary polyalcohols are a polyalkylene oxide (PAO), such as a polyalkylene glycols (PAG), including polymethylene glycol, polyethylene glycol (PEG), methoxypolyethylene glycol (MPEG) and polypropylene glycol; poly-vinyl alcohol (PVA); polyethylene-co-maleic acid anhydride; polystyrene-co-malic acid anhydride; dextrans including carboxymethyl-dextrans; celluloses, including methylcellulose, carboxymethylcellulose, ethylcellulose, hydroxyethylcellulose carboxyethylcellulose, and hydroxypropylcellulose; hydrolysates of chitosan; starches such as hydroxyethyl-starches and hydroxy propyl-starches; glycogen; agaroses and derivates thereof; guar gum; pullulan; insulin; xanthan gum; carrageenan; pectin; alginic acid hydrolysates; sorbitol; an alcohol of glucose, mannose, galactose, arabinose, gulose, xylose, threose, sorbose, fructose, glycerol, maltose cellobiose, sucrose, amylose, amylopectin; or mono propylene glycol (MPG).

"Poly amino acid" or "polyamino acid" means at least two amino acids linked by a peptide bond. Desirably, a poly amino acid is a peptide containing a repetitive amino acid sequence or a chain of the same amino acid (i.e., a homopolymer).

A "polycation" or "polycationic" refers to any macromolecular ion that carries multiple positive charges. Desirably, a polycation possesses free amine groups, for example, the polyamino acid poly-L-lysine. Other exemplary desirable polycations that contain free amine groups include natural polymers like chitosan (a β-(1-4)-linked copolymer of 2-amino-2-deoxy-β-D-glucan (GlcN) and 2-acetamido-2-deoxy-β-D-glucan (GlcNAc)), which contains free amine groups on the GlcN residues that can be cross-linked and act as the cation, and commercially available synthetic polymers that contain free amine groups such as branched polyethylenimine (PEI), Polyamine N7 (CAS 29320-38-5) and Ethylenediaminomethyl polystyrene (CAS 177987-93-8).

By "poly-L-lysine"and "PLL"is meant α-poly-L-lysine (alpha -poly-L-lysine; αPLL), ε-poly-L-lysine (epsilon-poly-L-lysine; εPLL; poly[imino[(2S)-2-amino-1-oxo-1,6-hexanediyl]]), or combinations and copolymers thereof. The lysine residues of poly-L-lysine are linked through a peptide bond between the carboxyl group and either the alpha (α-PLL) or epsilon (ε-PLL) amine group. Desirably the poly-L-lysine is α-poly-L-lysine. α-poly-L-lysine is chemically synthesized and can be obtained at various molecular weights, for example, 0.5 to 300 KDa. ε-poly-L-lysine is small natural homopolymer of the essential amino acid L-lysine that is produced by bacterial fermentation, e.g., ε-poly-L-lysine can be isolated from *Streptomyces albus*, and has an average molecular mass of approximately 4000 Da.

A "protein matrix" in the context of the present invention is a multimeric structure formed by cross-linking of protein molecules, forming links or direct bonds between two sites in the same protein molecule or between two sites on different protein molecules. A "carrier protein matrix" in the context of the present invention refers to a protein matrix formed by a crosslinking reaction performed with carrier proteins, wherein cross-links are formed between reactive sites in the same carrier protein molecule (resulting in intramolecular loop or fold structures) or between reactive sites on different carrier protein molecules (resulting in carrier protein polymers). The term "carrier protein/polycation matrix" as used herein refers to a protein matrix formed by a cross-linking reaction carried out in a mixture of carrier proteins and polycations, wherein cross-linking occurs at least within or between carrier protein molecules (resulting in a carrier protein matrix which may entrap polycations in the matrix), or wherein cross-linking occurs not only within or between carrier protein molecules but also within or between polycation molecules (resulting in a matrix that comprises crosslinked carrier protein and/or polycation monomers). The degree of cross-linking in forming a protein matrix may be controlled by judicious selection of cross-linking reactants and consideration of the reactive sites available for cross-linking on the monomeric components, controlling the amount of cross-linker used in the cross-linking reaction, controlling the reaction time, and the use of reagents to block reactive sites or quench the cross-linking reaction. Control of such parameters will affect the amount of antigen that can be entrapped, the rate at which entrapped antigen may dissociate from the protein matrix/antigen complex, and the size of the protein matrix particles formed. All of these qualities affect the immunogenicity of the protein matrix vaccine compositions of the present invention.

The term "reducing a Schiff base" refers to exposing azomethine or a compound of the formula $R_1R_2C=N-R_3$ (where $R_1$, $R_2$, and $R_3$ are chemical substructures, typically containing carbon atoms) to a reducing agent that saturates the double bond of the Schiff base with hydrogen atoms. Methods of chemical reduction are known to those skilled in the art.

The term "specifically binds" as used herein in reference to an antibody or a fragment thereof, means an increased affinity of an antibody or antibody fragment for a particular antigen, e.g., a protein or segment thereof, relative to an equal amount of any other antigen. An antibody or antibody fragment desirably has an affinity for its antigen that is least 2-fold, 5-fold, 10-fold, 30-fold, or 100-fold greater than for an equal amount of any other antigen, including related antigens, as determined using standard methods such as an enzyme linked immunosorbent assay (ELISA).

By "subject" is meant an animal that can be infected by a microbe. Desirably, a subject is a mammal such as a human, monkey, dog, cat, mouse, rat, cow, sheep, goat, or horse. A human subject may be an adult human, child, infant, toddler, or pre-pubescent child.

A "T cell-independent antigen" refers to an antigen which results in the generation of antibodies without the cooperation of T-helper lymphocytes. The T cell-independent antigen may directly stimulate B lymphocytes without the cooperation of T lymphocytes. Exemplary desirable T cell-independent antigens include capsular antigen poly-gamma-D-glutamic acid (PGA), alginic acid (alginate), dextran, polysaccharides (PS), poly amino acids, polyalcohols, and nucleic acids.

The terms "vaccine", "vaccine composition", and "immunogenic composition" are used herein to refer to any composition containing an antigen of interest which, when administered to a vertebrate subject elicits an immune response in the subject to said antigen. Although it is an objective of the invention to provide vaccines capable of eliciting a protective immune response (i.e., capable of protecting a vaccinated subject against a pathogen that naturally bears the antigen included in the vaccine), protective immunization, e.g., after a single administration, is not a quality that is inherent in the term "vaccine" or "vaccine composition" as used herein.

Protein matrix vaccine compositions of the present invention do not require covalent linkage between the antigen intended to elicit an immune response and the carrier protein and/or polycation used to form the matrix. This advantageously simplifies the preparation of protein matrix vaccine compositions, reducing the cost of their preparation compared to conjugate vaccine technology. Polysaccharide (PS)-protein conjugate vaccines have proved to be prohibitively expensive to produce and sell in the developing world. Conventional conjugate vaccines are difficult to produce cheaply because of the highly specialized chemistry required for each vaccine and the costs of production and purification of both PS antigen and carrier protein.

Vaccine compositions according to the present invention address a need for vaccines that can safely induce immunity against previously intractable antigens. Vaccine compositions as described herein may be monovalent (having a single antigen to induce an immune response) or multivalent (having multiple antigens to induce a multiplex immune response).

The meaning of other terms will be understood by the context in which they appear or as understood by skilled practitioners in the art, including practitioners in the fields of organic chemistry, pharmacology, microbiology, protein biochemistry, and immunology.

The present invention relates to an immunogenic composition comprising (1) one or more antigen of interest, (2) one or more carrier protein, and (3) one or more polycation, wherein said carrier protein and/or said polycation are cross-linked to form a protein matrix, and said antigen of interest is entrapped by said protein matrix. Such compositions may be readily prepared by admixing the antigen, carrier protein, and polycation components, then initiating a cross-linking reaction to cause cross-linking of the carrier protein and/or polycation. In alternative embodiments of the protein matrix vaccine production method, the order of addition of the components may be varied, although generally if a crosslinked protein matrix is formed prior to addition of the antigen of interest, the desired entrapment does not take place and the antigen remains a dissociated component. In preferred embodiments, the polycation and polysaccharide antigen are incubated together, followed by addition of the cros slinking agent, followed by addition of the carrier (matrix-forming) protein. The protein matrix vaccine compositions incorporating a polycation, e.g., α-PLL, according to the present invention improve the entrapment of antigens into the protein matrix with a resulting increase in immunogenicity compared to the antigen alone or to protein matrix vaccine compositions not incorporating a polycation.

The present invention features, in particular, protein capsular matrix vaccine compositions incorporating a polycation and methods of making and administering such compositions to provide immunity against antigens, particularly T cell-independent antigens or antigens which normally elicit weak immune responses, such as, e.g., polysaccharides (PS), polyalcohols, poly amino acids, and other organic polymers. The vaccine compositions of the invention have the potent immunological properties of typical PS-protein conjugate vaccines but desirably differ from conjugate vaccines in that no significant covalent atomic bonding is required to couple the antigen of interest, e.g., PS or capsular organic polymer, to the carrier protein/polycation. Rather, the antigen of interest, e.g., PS or capsular organic polymers, is entrapped within the carrier protein/polycation matrix. For example, a protein matrix may be formed by covalent cross-linking carrier protein molecules to themselves, to other carrier protein molecules and/or to the polycation in the presence of soluble antigen, e.g., PS or capsular organic polymers. Carrier proteins and/or polycations that are highly cross-linked to each other can form a matrix that can capture (entrap) an antigen and facilitate the uptake of that antigen by antigen presenting cells, with the resulting stimulation of antibody production by B-cells. As demonstrated herein, the level of antigen entrapment within the matrix is enhanced by the addition of a polycation, for example, poly-L-lysine, resulting in improved yields of PCMV particles and in turn resulting in enhanced immunogenicity of the PCMV compositions as compared to antigen alone or antigen/protein matrix complexes formed without the use of polycation.

Conceptually, the carrier protein/polycation matrix may be visualized in the form of a "mesh" that encloses the antigen or a series of "beads on a string" where the antigen is the "string", the protein or complexes of cross-linked proteins/polycation is the "bead" in this analogy. The antigen is entrapped within the carrier protein/polycation matrix if the carrier protein encircles the antigen to form a ring around the antigen or a 3-dimensional mesh in which the antigen is tangled within. Entrapment of antigen results in a desirable quantity of antigen becoming associated with an antigenic carrier without significant cross-linking occurring to bind antigen covalently to the carrier protein. Sufficient quantity of antigen and/or persistence of the association with carrier via entrapment enables protein matrix vaccines to exhibit enhanced immunogenicity in comparison to immunization with antigen alone or with antigen simply mixed with a carrier protein. Protein matrix vaccine compositions according to the present invention have been shown to achieve immunogenicity comparable to commercially available conjugate vaccines, in which antigen is covalently linked to a carrier.

In desirable embodiments, molecules of the carrier protein and/or polycation are covalently cross-linked. For example, a covalent linkage may contain a peptide bond between a primary amino group of a lysine side chain (e.g., on poly-L-lysine) and a carboxy group of an aspartate or glutamate side chain (e.g., on a carrier protein). In other desirable embodiments, covalent cross-links can be initiated using cross-linkers such as compounds of the formula OHC—R—CHO, where R is a linear or branched divalent alkylene of 1 to 12 carbon atoms, a linear or branched divalent heteroalkyl of 1 to 12 atoms, a linear or branched divalent alkenylene of 2 to 12 carbon atoms, a linear or branched divalent alkynylene of 2 to 12 carbon atoms, a divalent aromatic radical of 5 to 10 carbon atoms, a cyclic system of 3 to 10 atoms, $—(CH_2CH_2O)_qCH_2CH_2—$ in which q is 1 to 4, or a direct chemical bond linking two aldehyde groups. In preferred embodiments, the covalent linkage is formed using glutaraldehyde as a cross-linking agent, or alternatively such agents as m-maleimidobenzoyl-N-hydroxysuccinimide ester, carbodiimide, or bis-biazotized benzidine, bis[sulfosuccinimidyl]suberate, or dimethyl adipimidate may be used. Although not required in the formation of a protein matrix vaccine composition, the antigen of interest may be covalently bound to the carrier protein, for example, to an extent that is incidental to the formation of the cross-linked carrier protein matrix, e.g., due to unblocked reactive groups or terminal amino or carboxyl groups or hydroxyl groups that may exist on the antigen. In general, covalent linkage of antigen to carrier is not an object in the formation of protein matrix vaccines. For the purposes of the invention, protein matrix vaccines are vaccine compositions wherein no more than 50% of the antigen is covalently linked to carrier protein. The amount of incidental antigen cross-linking may be calculated stoichiometrically by considering the proportion of sites in the antigen that are able to participate in a cross-linking reaction, i.e., taking into account the reactive groups of the cross-linking reagent(s) used, the amount of reagent(s) and other reactants (e.g., carrier protein, polycation) used, and whether cross-linking reactions are allowed to go to completion (e.g., whether all of a cross-linking reagent is consumed during the reaction). The amount of cross-linked antigen in a protein matrix vaccine composition may also be measured, e.g., by mass spectrometry analysis of a PCMV composition for carbohydrate/lysine crosslinks.

In desirable embodiments, the antigen and the carrier protein/polycation matrix are non-covalently associated. Such non-covalent association may involve hydrophobic interaction, ionic interaction, van der Waals interaction, or hydrogen bonding; or the antigen may be physically or sterically enclosed within the protein matrix, such that dissociation of antigen from the matrix is prevented or retarded. Non-covalent association can include physical geometric configurations that non-covalently associate (entrap) antigen with protein complexes (i.e., as in the "bead on a string" analogy above).

Vaccine compositions of the invention may be prepared using any of many possible linkers to cros slink any of many possible carrier proteins and/or polycations in the presence of any antigen of interest. Exemplary and preferred linkers, carrier proteins, polycations and antigens of interest are discussed herein.

Polysaccharides (PS) are polymers of saccharides (sugars). PS derived from microbial capsules are the primary antigenic components involved in protective immunity against encapsulated bacterial pathogens such as *Neisseria meningitidis, Streptococcus pneumoniae, Salmonella Typhi*, and *Haemophilus influenzae* Type B. Immunization of adolescents and adults with vaccines based on microbial polysaccharides has been successful in reducing disease burden, but has proven less effective in providing protective immunity to infants and young children (i.e., children less than 24 months of age). Young children have not yet developed a mature adaptive immune repertoire and T cell-independent antigens such as capsular PS are poorly immunogenic and do not lead to long-term protective immune responses (i.e., an immunological memory response) in such young vaccine recipients.

A T cell-independent antigen such as polysaccharide can be converted to a T cell-dependent antigen by chemical coupling of polysaccharide to protein. This process, known as "conjugation", involves the formation of covalent bonds between atoms in the polysaccharide structure and side chain atoms of amino acids present in the "carrier" protein. Such "conjugate vaccines" more efficiently promote the induction of B-cell maturation and isotype switching, leading to much higher levels of antibody with the correct anti-PS protective profile. Protective antibodies have high affinity for their polysaccharide antigens, and typically are of the Immunoglobulin G (IgG) subclass, a long-lived antibody with complement fixing and opsonization effector activity.

A T cell-independent antigen generally does not stimulate lasting immunity, i.e., the production of IgG antibodies, but may stimulate the production of less potent, poorer binding, and more temporary, IgM antibodies. As such, polysaccharide antigens alone do not typically produce booster responses of IgG. However, polysaccharides do produce booster responses if primary immunization is performed with a PS-protein conjugate, because memory cells induced by the conjugate have already been programmed to produce IgG. Indeed, the booster response in vaccinated animals or humans is thought to mimic the protective response due to exposure to a microbe displaying the PS; this long term memory is critical for a vaccine to work in providing protective immunity to immunized subjects years after their immunization. Thus, PS-protein conjugates are valued for (1) their ability to induce high levels of IgG against PS antigens, and (2) their ability to induce memory immune responses against PS antigens. Polysaccharide antigens alone typically do not display these properties and thus are inferior antigens. The difficulty in synthesizing conjugate vaccines and their cost of production has slowed the development of conjugate vaccines for many bacterial diseases where a protective immune response to a polysaccharide antigen is sought.

Other T cell-independent antigens include homopolymers of amino acids, such as poly-gamma-D-glutamic acid (PGA), and polyalcohols. Most biopolymers are T cell-independent antigens. Polymers can crosslink immunoglobulin (Ig) receptors on B-cells that recognize them due to the repetitive nature of their chemical structures (and thus epitopes). Thus polymers can activate B-cells for production of anti-polymer IgM in the same way that polysaccharides do. For example, an amino acid homopolymer, poly-gamma-D-glutamic acid (PGA) of *Bacillus anthracis*, is a capsular polymer that is poorly immunogenic and also a T cell-independent antigen. Vaccines composed of PGA conjugated to protein carriers are highly immunogenic, able to induce anti-PGA IgG, and immunological memory to PGA. Hence, most polymers respond like PS in terms of their immunogenicity because they cannot be processed and displayed in the context of MHC-II and thus cannot recruit T cell help. An exception is found in some naturally-occurring polymers that interact with another class of receptor termed Toll-like receptors (TLRs). Once activated, TLRs can induce production of cytokines by host cells and produce changes in the adaptive immune response. Some PS are covalently attached to TLR ligands or contaminated with such ligands. For example, lipopolysaccharides (LPS) are PS that are highly immunogenic and induce IgG and memory responses; the lipid A moiety of LPS is a TLR ligand and may be responsible for the immunological properties.

Conventional conjugate vaccines are difficult to produce cheaply because costs of production and purification of both PS antigen and carrier protein and the specific chemistry involved in each polysaccharide-protein conjugation. Usually both need to be quite pure before conjugation chemistry can be performed with a reasonable coupling efficiency. Typically, coupling chemistry must be specifically developed for various PS that is unique for the chemistry of the PS and the carrier proteins that have been selected. This coupling chemistry introduces functional groups in the PS that then can be linked to carrier protein typically through the epsilon amino side chains of lysine residues. The chemical modification of PS to introduce such coupling groups can destroy epitopes on the PS and introduce new epitopes (e.g., associated with the linker or modified saccharide groups) whose significance can only be assessed by performing careful immunological analysis. Furthermore, for conventional PS-protein conjugate vaccines, the size of the PS, the number of PS molecules bound per protein carrier molecule, the nature of the carrier selected, and the type of linkage chemistry can all affect immunogenicity of the conjugate vaccine. As such, for example, in the case of pneumococcal disease where each of the 90+ known serotypes has a different PS structure (Bentley et al., PLOS Genetics 2(3): e31 262-269, 2006), one single conjugation method is not appropriate for all serotypes. Reproducibly synthesizing conjugate vaccines with reproducible immunological properties involves careful control of the size of the PS, the number of PS molecules bound per protein carrier molecule, the nature of the carrier selected, and the type of linkage chemistry. This, in turn, dramatically increases the cost of manufacture of conjugate vaccines.

The emergence of antibiotic resistance highlights the urgency for the development of safe and effective vaccines. Making vaccines widely available, especially for those in developing countries, requires that the manufacture of vaccines also to be cost-effective. Incorporation of combined conjugate vaccines against many polysaccharide antigens from different serotypes of one or more bacterial species into the childhood immunization regimen would simplify vaccine administration in that high-risk population. However, current conjugate vaccine technology is not cost-effective and thus, combination conjugate vaccines are virtually impossible to deliver to the developing world because of the high cost.

In desirable embodiments, the immunogenic vaccine compositions of the invention are protein capsular matrix vaccines (PCMV) where one or more bacterial capsular components are entrapped in a cross-linked carrier protein and/or polycation matrix. PCMVs can be produced more easily than conjugates because the antigen of interest, e.g., bacterial capsule polysaccharides, need not be hydrolyzed to smaller fragments and multiple antigens can be entrapped in a protein matrix simultaneously.

Because the method of making vaccines of the invention does not require any knowledge of the chemistry of the antigen of interest, e.g., a capsular polysaccharide, the method does not depend on the need to develop cross-linking chemistry that is compatible with the chemistry of the antigen of interest and the carrier protein. While it is possible that some antigens may interact with the cross-linker, this should not detract from the efficacy of the vaccine, because the unintended cross-linking of the antigen of interest and the carrier protein would be expected to have immunogenic properties similar to conjugates. In the vaccines of the invention, however, cross-linking of the antigen of interest to the carrier protein is not a requirement for the vaccine to be immunologically effective. This is in sharp contrast to conventional conjugate vaccines. The vaccines of the invention desirably have at least, e.g., 1%, 5%, 10%, 20%, 30%, 40%, 50%, 60%, 70%, 80%, 90%, 95%, 98%, or even 100% of the carrier proteins cross-linked and no more than, e.g., 50%, 40%, 30%, 25%, 20%, 15%, 10%, 5%, or 1% of the antigen of interest cross-linked to the carrier protein. Desirably, no more than 10% of antigens are cross-linked to the carrier proteins and at least 50% of carrier proteins are cross-linked.

As discussed herein, the protein matrix vaccine compositions which incorporate a polycation have increased antigen entrapment and corresponding higher immunogenicity compared to compositions comprised of the antigen alone, simple antigen/carrier admixtures, and even antigen/protein matrix vaccine compositions not incorporating a polycation in accordance with the teachings herein. As discussed herein, polysaccharide capsules of bacteria are composed of repeating sugars and for many pathogenic bacterial capsules are negatively charged. The negative charge may assist in preventing phagocytosis by host immune cells through charge repulsion or by presenting a larger more inhibitory capsule. Weinger et al., *PLosPathogens*, 5: 1-9 (2009). This same charge repulsion may also be occurring with the matrix protein(s), resulting in poor polysaccharide entrapment. To counteract this negative charge a polycation, for example, poly-L-lysine (PLL), can be added to PCMV reactions. For example, as discussed herein, the addition of 0.04% α-PLL to the Vi-CRM197 PCMV reaction increased Vi polysaccharide entrapment from 5% to >20% (FIG. 1).

Control of particle size can improve the immunogenicity of protein matrix vaccines. In desirable embodiments of the invention, the antigen/carrier protein/polycation matrix complex has a mean particle size diameter above 50 nm. Desired size particles can be fractionated by any suitable means, including size exclusion chromatography (SEC), followed by pooling the larger sized particles and discarding smaller sized particles and/or non-entrapped polysaccharide. Alternatively, use of filter membranes with well-chosen molecular weight cutoffs could be used to remove smaller-sized particles while retaining particles of the desired size. The elimination of lower molecular weight species (e.g., <50 nm diameter species) or the selection of protein matrix particle sizes of the composition that include particle sizes greater than at least 50 nm diameter can be accomplished by any known means in the art, for example, chromatography, including size-exclusion chromatography (SEC), gel-filtration chromatography, or gel-permeation chromatography. Gel electrophoresis techniques could also be used.

The methods of making vaccines described herein do not result in the extensive modification of the antigen of interest, e.g., a capsular polymer. The antigen generally remains in the same state with a possible modification being, e.g., the reduction of reducing sugars for PS capsules that carry such groups at the end of the polymer chains. Such minor modifications are unlikely to affect immunogenicity of most capsular PS because the end sugars are 100-10,000 times less abundant than the internal residues in the polymer. In contrast, for conventional conjugate vaccines, it is usually necessary to introduce linker groups into the antigen, e.g., a capsular polymer, that serve as the point of covalent attachment of the carrier protein. For example, the introduction of reactive groups into a PS can result in destruction of capsular epitopes and generation of novel epitopes that might be undesirable in a vaccine product because of their unknown immunological cross-reactivity with host self-epitopes.

The methods of making vaccines described herein are less complex than conjugate vaccine technology because its chemistry depends only on the cross-linking chemistry of the carrier protein (e.g., DNI, cholera toxin B subunit, diphtheria toxoid, tetanus toxoid or Fragment C, or *Escherichia coli* beta-galactosidase) and/or polycation (e.g., α-poly-L-lysine and ε-poly-L-lysine). For example, while the capsular polymer affects the rate of cross-linking when mixed with DNI, it does not affect the pattern or extent of cross-linking which is governed more by the protein being used, its concentration, and the concentration of the cross-linking agent (e.g., glutaraldehyde) added. These parameters can readily be adjusted, thereby reducing the time and effort required to make the vaccine, and saving expense.

The methods of making PCMV compositions described herein can be used with any antigen, e.g., a capsular polymer or any biopolymer with few if any amino groups, and any carrier protein and/or polycation that can be crosslinked, e.g., carrier proteins not having critical epitopes that can be destroyed upon cross-linking or chemical reduction. Carrier proteins that may be used in the methods described herein desirably have at least 2 lysine residues or other residues that are unblocked and that can be cross-linked by chemical modification. Tetanus toxoid is one possible carrier protein. This toxin is rendered non-toxic by treatment with formaldehyde, a reagent that reacts with amino groups of proteins. Other desirable carrier proteins include the cholera toxin B subunit (available from SBL Vaccin AB), diphtheria toxoid or CRM197, tetanus toxoid or Fragment C (available from Sigma Aldrich), DNI, or beta-galactosidase from *Escherichia coli* (available from Sigma Aldrich).

Current multivalent conjugate vaccines are made by synthesis of individual conjugate vaccines first, followed by their mixing to produce a "cocktail" conjugate vaccine (e.g., the Wyeth hepta-valent pneumococcal vaccine, Prevnar®-7, GlaxoSmithKline's 10-valent pneumoccal vaccine Synflorix®, and Pfizer's 13-valent vaccine Prevnar®-13). The present invention's methods of making vaccines can be used to make multivalent vaccines by mixing chemically different antigens, e.g., capsular organic polymers, together before crosslinking the carrier protein and/or polycation, e.g., with glutaraldehyde or other cros slinking agent, or by mixing specific vaccines of the invention that were synthesized separately. This flexibility provides significant advantages over conventional methods of manufacturing multivalent vaccines which should considerably lower the cost of goods.

Exemplary vaccines of the invention discussed in the examples performed comparably to conjugate vaccines despite the fact that these vaccines were synthesized by a method that is not predicted to generate any covalent bonds between antigen molecules and the carrier protein. Glutaraldehyde reacts primarily with amino side chains of proteins typified by the epsilon amino group of lysine residues. Polysaccharide antigens are essentially non-reactive with glutaraldehyde and other aldehyde-functional reagents because they contain few free amino groups (any amino side chains are typically acetylated) to react with glutaraldehyde or aldehyde-functional crosslinkers (e.g., OCH—R—CHO, discussed supra). Therefore such antigens are well suited to PCMV formation, where less than 50% of antigen is crosslinked directly to a carrier protein. As seen in the examples below, the immune responses generated by PCMVs, which compared favorably to conjugate controls, indicate that PS molecules were molecularly entrapped within a cross-linked matrix of DNI protein molecules.

According to a non-limiting model, the entrapment acts to deliver the protein matrix vaccine composition to B cells that bind such matrices via Ig receptors that recognize the polymer antigen. Once taken up inside these B cells, the matrices are degraded in a manner similar to conventional conjugate vaccines, resulting in carrier protein-derived peptides that are displayed on MHC class II molecules of the B cells. This in turn recruits T-helper cells and thus leads to the expansion and maturation of such B cells to become IgG producing plasma and 'memory' cells specific to the antigen. Thus, according to the non-limiting model PCMVs work like protein-conjugate capsular vaccines immunologically but are distinct because PCMVs lack significant covalent bonding between the carrier protein and the capsular polymers.

The vaccine compositions of the invention, including PCMVs, may be used in combination, for example, in pediatric vaccines. In addition, the vaccines of the invention may be used to vaccinate against, for example, pneumococcal infection, streptococcal (groups A and B) infection, *Haemophilus influenzae* type B ("HiB") infection, meningococcal (e.g., *Neisseria meningitides*) infection, and may be used as O antigen vaccines from Gram negative bacteria (e.g., *Pseudomonas aeruginosa, Francisella tularensis* (Thirumalapura et al., J. Med. Microbiol. 54:693-695, 2005; Vinogradov and Perry, Carbohydr. Res. 339:1643-1648, 2004; Vinogradov et al., Carbohydr. Res. 214:289-297, 1991), *Shigella* species, *Salmonella* species, *Acinetobacter*-species, *Burkholderia* species, and *Escherichia coli*.

Vaccines of the invention may be made using any linkers, such as, e.g., those described herein, to crosslink any carrier protein and/or polycation, such as, e.g., those described herein, in the presence of one or more antigens of interest, such as, e.g., those described herein. If one antigen of interest is used, the protein matrix vaccine of the invention is said to be monovalent. If more than one antigen of interest is used, the protein matrix vaccine of the invention is said to be multivalent. If a microbial capsular polymer or polysaccharide is the antigen of interest, the protein matrix vaccine of the invention is said to be a protein capsular matrix vaccine (PCMV).

Linkers

Cross-linking agents useful to crosslink carrier proteins and/or polycations are well known in the art and include glutaraldehyde, m-maleimidobenzoyl-N-hydroxysuccinimide ester, carbodiimide, and bis-biazotized benzidine.

General methods and moieties for directly crosslinking carrier proteins, using a homobifunctional or a heterobifunctional linker are described, for example, by G. T. Hermanson, *Bioconjugate Techniques* (Academic Press, 1996) and Dick and Beurret, "Glycoconjugates of Bacterial Carbohydrate Antigens," in *Conjugate Vaccines* (Cruse and Lewis, eds.) (*Contrib. Microbiol. Immunol. Basel, Karger*, 1989), vol. 10, pp. 48-114. For example, with a carrier protein possessing 'n' number of lysine moieties, there are, theoretically, 'n+1' primary amines (including the terminal amine) available for reaction with an exemplary crosslinker's carboxylic group. Thus, using this direct conjugation procedure the product is limited to having 'n+1' amide bonds formed.

The linker employed in desirable embodiments of the present invention is, at its simplest, a bond connecting two carrier proteins, a bond connecting two polycations, a bond connecting two sites of the same carrier protein or polycation, or a bond connecting carrier proteins and polycations. The linker can have a linear, cyclic, or branched molecular skeleton, with pendant groups which bind covalently to two carrier proteins and/or polycations, (A) and (B). Any given carrier protein may be linked to more than one carrier protein and/or to a polycation, such that a matrix of interconnected carrier proteins/polycations is created, in which an antigen of interest may be entrapped.

The term "linkage group" refers to the covalent bond that results from the combination of reactive moieties of linker (L) with functional groups of (A) or (B). Examples of linkage groups include, without limitation, ester, carbamate, thioester, imine, disulfide, amide, ether, thioether, sulfonamide, isourea, isothiourea, imidoester, amidine, phosphoramidate, phosphodiester, thioether, and hydrazone.

The linking of (A) with (B) is achieved by covalent means, involving bond (linkage group) formation with one or more functional groups located on (A) and (B). Examples of chemically reactive functional groups which may be employed for this purpose include, without limitation, amino, hydroxyl, sulfhydryl, carboxyl, carbonyl, thioethers, guanidinyl, imidazolyl, and phenolic groups, all of which are present in naturally-occurring amino acids in many carrier proteins.

The covalent linking of (A) with (B) may therefore be effected using a linker (L) which contains reactive moieties capable of reaction with such functional groups present in (A) and (B). The product of this reaction is a linkage group which contains the newly formed bonds linking (L) with (A) and (L) with (B). For example, a hydroxyl group of (A) may react with a carboxylic acid group of (L), or an activated derivative thereof, vide infra, resulting in the formation of an ester linkage group.

Examples of moieties capable of reaction with sulfhydryl groups include α-haloacetyl compounds of the type $XCH_2CO$— (where X=Br, Cl, or I), which show particular reactivity for sulfhydryl groups, but which can also be used to modify imidazolyl, thioether, phenol, and amino groups as described by, for example, Gurd, *Methods Enzymol.*, 11:532 (1967). N-Maleimide derivatives are also considered selective towards sulfhydryl groups, but may additionally be useful in coupling to amino groups under certain conditions. Reagents such as 2-iminothiolane (Traut et al., *Biochemistry*, 12:3266 (1973)), which introduce a thiol group through conversion of an amino group, may be considered as sulfhydryl reagents if linking occurs through the formation of disulphide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type XCH$_2$CO— (where X=Cl, Br or I as described by, for example, Wong (*Biochemistry,* 24:5337 (1979));
(ii) N-maleimide derivatives, which may react with amino groups either through a Michael type reaction or through acylation by addition to the ring carbonyl group as described by, for example, Smyth et al. (*J. Am. Chem. Soc.,* 82:4600, 1960 and *Biochem. J.,* 91:589 (1964));
(iii) aryl halides such as reactive nitrohaloaromatic compounds;
(iv) alkyl halides, as described by, for example, McKenzie et al. (*J. Protein Chem.,* 7:581 (1988));
(v) aldehydes and ketones capable of Schiff's base formation with amino groups, the adducts formed usually being stabilized through reduction to give a stable amide;
(vi) epoxide derivatives such as epichlorohydrin and bisoxiranes, which may react with amino, sulfhydryl, or phenolic hydroxyl groups;
(vii) chlorine-containing derivatives of s-triazines, which are very reactive towards nucleophiles such as amino, sulfhydryl, and hydroxyl groups;
(viii) aziridines based on s-triazine compounds detailed above as described by, for example, Ross (*J. Adv. Cancer Res.,* 2:1 (1954)), which react with nucleophiles such as amino groups by ring opening;
(ix) squaric acid diethyl esters as described by, for example, Tietze (*Chem. Ber.,* 124:1215 (1991)); and
(x) α-haloalkyl ethers, which are more reactive alkylating agents than normal alkyl halides because of the activation caused by the ether oxygen atom, as described by, for example, Benneche et al. (*Eur. J. Med. Chem.,* 28:463 (1993)).

Representative amino-reactive acylating agents include:
(i) isocyanates and isothiocyanates, particularly aromatic derivatives, which form stable urea and thiourea derivatives respectively;
(ii) sulfonyl chlorides, which have been described by, for example, Herzig et al. (*Biopolymers,* 2:349 (1964));
(iii) acid halides;
(iv) active esters such as nitrophenylesters or N-hydroxysuccinimidyl esters;
(v) acid anhydrides such as mixed, symmetrical, or N-carboxyanhydrides;
(vi) other useful reagents for amide bond formation as described by, for example, M. Bodansky (*Principles of Peptide Synthesis,* Springer-Verlag, 1984);
(vii) acylazides, e.g., where the azide group is generated from a preformed hydrazide derivative using sodium nitrite, as described by, for example, Wetz et al. (*Anal. Biochem.,* 58:347 (1974)); and
(viii) imidoesters, which form stable amidines on reaction with amino groups as described by, for example, Hunter and Ludwig (*J. Am. Chem. Soc.,* 84:3491 (1962)).

Aldehydes, such as, e.g., glutaraldehyde, and ketones may be reacted with amines to form Schiff's bases, which may advantageously be stabilized through reductive amination. Alkoxyamino moieties readily react with ketones and aldehydes to produce stable alkoxyamines as described by, for example, Webb et al. (*Bioconjugate Chem.,* 1:96 (1990)).

Examples of reactive moieties capable of reaction with carboxyl groups include diazo compounds such as diazoacetate esters and diazoacetamides, which react with high specificity to generate ester groups as described by, for example, Herriot (*Adv. Protein Chem.,* 3:169 (1947)). Carboxylic acid modifying reagents such as carbodiimides, which react through O-acylurea formation followed by amide bond formation, may also be employed.

The functional groups in (A) and/or (B) may, if desired, be converted to other functional groups prior to reaction, for example, to confer additional reactivity or selectivity. Examples of methods useful for this purpose include conversion of amines to carboxylic acids using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxylic acids using reagents such as α-haloacetates; conversion of thiols to amines using reagents such as ethylenimine or 2-bromoethylamine; conversion of carboxylic acids to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of (A) with a reactive chemical group of (B) without introducing additional linking material may, if desired, be used in accordance with the invention. Examples include compounds in which (L) represents a chemical bond linking an oxygen atom of (A) to a carbonyl or thiocarbonyl moiety present in (B), such that the linkage group is an ester or thioester. For example, an amino group (A) can be linked to a carboxyl group (B) by using carbodiimide chemistry yielding A-L-B where L is an amide bond or RC(:O) linked to N-R where R is the carbon chain derived from amino acid side chains of the same or two different protein molecules. Most commonly, however, the linker includes two or more reactive moieties, as described above, connected by a spacer element. The presence of a spacer permits bifunctional linkers to react with specific functional groups within (A) and (B), resulting in a covalent linkage between these two compounds. The reactive moieties in a linker (L) may be the same (homobifunctional linker) or different (heterobifunctional linker, or, where several dissimilar reactive moieties are present, heteromultifunctional linker), providing a diversity of potential reagents that may bring about covalent attachment between (A) and (B).

Spacer elements typically consist of chains which effectively separate (A) and (B) by a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, or —(CH$_2$CH$_2$O)$_n$CH$_2$CH$_2$—, in which n is 1 to 4.

The nature of extrinsic material introduced by the linking agent may have a bearing on the pharmacokinetics and/or activity of the ultimate vaccine product. Thus it may be desirable to introduce cleavable linkers, containing spacer arms which are biodegradable or chemically sensitive or which incorporate enzymatic cleavage sites.

These cleavable linkers, as described, for example, in PCT Publication WO 92/17436 (hereby incorporated by reference), are readily biodegraded in vivo. In some cases, linkage groups are cleaved in the presence of esterases, but are stable in the absence of such enzymes. (A) and (B) may, therefore, advantageously be linked to permit their slow release by enzymes active near the site of disease.

Linkers may form linkage groups with biodegradable diester, diamide, or dicarbamate groups of the formula:

—(Z$^1$)$_o$—(Y$^1$)$_u$—(Z$^2$)$_s$—(R$_{11}$)—(Z$^3$)$_t$—(Y$^2$)$_v$—(Z$^4$)$_p$— wherein each of Z$^1$, Z$^2$, Z$^3$, and Z$^4$ is independently selected from O, S, and NR$_{12}$ (where R$_{12}$ is hydrogen or an alkyl group); each of Y$^1$ and Y$^2$ is independently selected from a carbonyl, thiocarbonyl, sulphonyl, phosphoryl or similar acid-forming group; o, p, s, t, u, and v are each independently 0 or 1; and R$_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —(CH$_2$CH$_2$O)$_q$CH$_2$CH$_2$— in which q is 1 to 4, or a chemical bond linking —(Z$^1$)$_o$—(Y$^1$)$_u$—(Z$^2$)$_s$—(R$^{11}$)—(Z$^3$)$_t$—(Y$^2$)$_v$—(Z$^4$)$_p$—.

Exemplary desirable linkers (L) used in the present invention may be described by any of formulas I-II:

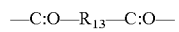
—C:O—R$_{13}$—C:O—  I

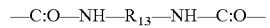
—C:O—NH—R$_{13}$—NH—C:O—  II where the linker is covalently attached to both an oxygen atom (A) and an oxygen atom of (B). Accordingly, linker (L) of formulas I-II are attached to carrier proteins (A) and (B) via dipyran, ester, or carbamate linkage groups. In these embodiments, R$_{13}$ represents a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —(CH$_2$CH$_2$O)$_n$CH$_2$CH$_2$— in which n is 1 to 4, or a chemical bond linking two nitrogens or two carbonyls.

Linkers designed to form hydrazone linkages have the chemical formula III:

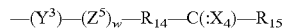
—(Y$^3$)—(Z$^5$)$_w$—R$_{14}$—C(:X$_4$)—R$_{15}$  III where Z$^5$ is selected from O, S, or NR$_{16}$; R$_{16}$ is hydrogen or an alkyl group; R$_{15}$ is selected from hydrogen, an alkyl, or a heteroalkyl; Y$^3$ is selected from a carbonyl, thiocarbonyl, sulphonyl, phosphoryl, or a similar acid-forming group covalently bound to an oxygen atom of (A); w is 0 or 1; R$_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —(CH$_2$CH$_2$O)$_n$CH$_2$CH$_2$—, in which n is 1 to 4, or a chemical bond linking —(Y$^3$)—(Z$^5$)$_w$— to and X$_4$ is a hydrazone resulting from the condensation reaction of (B) containing a hydrazide group and the precursor to linker II, in which X$_4$ is the oxygen atom of a ketone or aldehyde group.

Carrier Proteins

In general, any carrier protein that can entrap an antigen under physiological conditions may be used in the present invention. Desirably, the antigen is entrapped in a complex with cross-linked matrix of the carrier protein and/or polycation in the absence of significant covalent bonding between the antigen and the carrier protein/polycation matrix. Absence of significant covalent bonding, refers to no more than 50% of the antigen being covalently bonded to a carrier protein and/or polycation. In desirable embodiments, no more than 40%, 30%, 10%, or 5% of the antigen is covalently bonded to a carrier protein and/or polycation. The antigen/carrier protein/polycation complex may contain another compound, such as alum.

Carrier proteins used in the vaccines of the invention desirably are proteins that, either alone or in combination with an antigen, elicit an immune response in a subject. Desirably, the carrier protein contains multiple MCH class II-restricted epitopes recognized by a helper T cell. Desirably, the epitopes are capable of inducing a T$_h$ cell response in a subject and induce B cells to produce antibodies against the antigen of interest and the microbes from which the antigen is derived. Epitopes as used in describing this invention, include any determinant on an antigen that is responsible for its specific interaction with an antibody molecule or fragment thereof. Epitopic determinants usually consist of chemically active surface groupings of molecules such as amino acids or sugar side chains and have specific three-dimensional structural characteristics as well as specific charge characteristics. To have immunogenic properties, a protein or polypeptide generally is capable of stimulating T$_h$ cells. However, a carrier protein that lacks an epitope recognized by a T$_h$ cell may also be immunogenic.

By selecting a carrier protein which is known to elicit a strong immune response (i.e., is highly immunogenic) and to contain "universal" or "broad range" or "pan DR" helper T cell epitopes (see, e.g., WO 2008/057529), a diverse population of subjects can be treated by a protein matrix vaccine composition described herein. The carrier protein desirably is sufficiently foreign to elicit a strong immune response to the vaccine. Typically, the carrier protein used is a molecule that is capable of stimulating immunogenicity to the antigen of interest. In a desirable embodiment, a carrier protein is one that is inherently highly immunogenic. Thus a carrier protein that has a high degree of immunogenicity and is able to maximize antibody production to the antigen(s) complexed with it is desirable.

Various carrier proteins useful in the practice of the invention will include, e.g., toxins and toxoids (chemical or genetic), which may or may not be mutant, such as anthrax toxin, PA and DNI (PharmAthene, Inc.), diphtheria toxoid (Massachusetts State Biological Labs; Serum Institute of India, Ltd.) or CRM197, tetanus toxin, tetanus toxoid (Massachusetts State Biological Labs; Serum Institute of India, Ltd.), tetanus toxin fragment Z, exotoxin A or mutants of exotoxin A of *Pseudomonas aeruginosa*, bacterial flagellin, pneumolysin, an outer membrane protein of *Neisseria meningitidis* (strain available from the ATCC (American Type Culture Collection, Manassas, Va.)), *Pseudomonas aeruginosa* Hcp1 protein, *Escherichia coli* heat labile enterotoxin, shiga-like toxin, human LTB protein, a protein extract from whole bacterial cells, and any other protein that can be cross-linked by a linker. Desirably, the carrier protein is the cholera toxin B subunit (available from SBL Vaccin AB), diphtheria toxoid or CRM197 (Connaught, Inc.), tetanus toxoid or Fragment C (available from Sigma Aldrich), DNI, or beta-galactosidase from *E. coli* (available from Sigma Aldrich). Other desirable carrier proteins include bovine serum albumin (BSA), P40, and chicken riboflavin. (Unless otherwise indicated, the exemplary carrier proteins are commercially available from Sigma Aldrich.) Other exemplary carrier proteins are MAPs (multi-antigenic peptides), which are branched peptides. By using a MAP, crosslinking density is maximized because of multiple branched amino acid residues. A desirable amino acid residue for crosslinking purposes, which can be used to form a MAP, is, but is not limited to, lysine, having a free amino group on its side chain.

Both BSA and keyhole limpet hemocyanin (KLH) have commonly been used as carriers in the development of vaccines when experimenting with animals. Carrier proteins which have been used in the preparation of therapeutic vaccines include, but are not limited to, a number of toxins of pathogenic bacteria and their toxoids. Examples include diphtheria and tetanus toxins and their medically acceptable corresponding toxoids. Other candidates are proteins antigenically similar to bacterial toxins referred to as cross-reacting materials (CRMs). Carrier proteins useful in the practice of the invention may also include any protein not derived from humans and not present in any human food substance.

In desirable embodiments of the invention, proteins that form ring-like structures are used for PCMV production. Such proteins include the Hcp1 protein of *Pseudomonas aeruginosa*, the nontoxic "B subunits" of cholera toxin, the heat-labile enterotoxin of *Escherichia coli*, and shiga-like toxin. Such ring-like protein complexes can form structures where the linear PS chains penetrate the central channel of these ring-shaped protein complexes. After protein cross-linking, such complexes are predicted to be particularly stable. Structural data of the proteins suggest these central channels are large enough for PS chains to enter easily. For example, the central channel of the Hcp1 hexameric ring is 42 Angstroms which is wide enough to easily accommodate several polysaccharide chains of 5.5 Angstroms in width (Mougous et al., *Science*, 312(5779):1526-1530 (2006)). Alternatively, protein rings may be assembled around the polysaccharide (e.g., from subunits of a monomeric carrier protein that naturally assemble into rings under particular physical chemical conditions). Such monomeric proteins that can assemble into rings are known in the art and include, for example, pneumolysin (Walker et al., *Infect. Immun.*, 55(5):1184-1189 (1987); Kanclerski and Mollby, *J. Clin. Microbiol.*, 25(2):222-225 (1987)), listeriolysin O (Kayal and Charbit, *FEMS Microbiol. Rev.*, 30:514-529 (2006); Mengaud et al., *Infect. Immun.*, 55(12):3225-3227 (1987)), DNI, anthrax PA, Hcp1, cholera toxin B subunit, shiga toxin B subunit, flagellin, and numerous related molecules known in the art and made by various microorganisms.

In another desirable embodiment, Toll-like receptor (TLR) agonists are used as carrier proteins. Toll-like receptor (TLR) activation is important in shaping the adaptive immune response and may play a role in affinity maturation of the antibody response, isotype switching, and immunological memory. Flagellin (FLA) of *Vibrio cholerae* is a TLR agonist. FLA protein has been purified from recombinant *Escherichia coli* and shown to be a potent TLR activator in an IL-6 macrophage induction assay. In addition, a well-conserved *Streptococcus pneumoniae* protein called "Pneumolysin" has also been shown to activate TLR4 and, additionally, is a protective antigen. Thus, this protein can also be used as a protein matrix carrier protein.

Further, outer membrane protein (OMP) mixtures (e.g., the OMPs of *Neisseria meningitidis*) are used as the carrier protein for HIB conjugate vaccine produced by Merck and protein extracts from whole *Streptococcus pneumoniae* bacterial cells have been shown to be at least partially protective in animal infection models. In desirable embodiments of the invention, these protein mixtures may be used as carrier proteins.

In a desirable embodiment, the vaccine composition is made using a carrier protein that has, e.g., at least two lysine residues or other residues that are unblocked and that can be cross-linked by chemical modification. In other desirable embodiments, the carrier protein is a multimer (e.g., one containing at least 5 subunits).

In another embodiment, DNI is used as the carrier protein because it is nontoxic, leaving no need to render it less toxic before use. Furthermore, the use of DNI is desirable because DNI may also induce a protective immune response to *B. anthracis*, in addition to the protective immune response elicited to the antigen of interest. Also, DNI has no internal disulfide bonds. Such bonds are susceptible to borohydride reduction, which could denature the protein and result in loss of epitopes that induce anthrax toxin neutralizing antibody.

Antigens of Interest

The vaccine compositions of the invention and methods of making and administering such vaccines can be used for any antigen of interest and is especially advantageous for use with antigens which are not by themselves strongly immunogenic. This includes, e.g., a large number of polysaccharide, polyalcohol, or poly amino acid antigens. Desirably, the antigen of interest carries no primary groups that can be destroyed by the chemical reactions employed by the method of making vaccines, e.g., the denaturing of an antigen caused by the destruction of antigen disulfide bonds by borohydride reduction. Exemplary antigens of interest include but are not limited to organic polymers such as polysaccharides (e.g., polysaccharides having at least 18 residues), phosphopolysaccharides, polysaccharides with amino sugars with N-acetyl substitutions, polysaccharides containing sulfonylated sugars, other sulfate-modified sugars, or phosphate-modified sugars, polyalcohols, poly amino acids, teichoic acids, O polysaccharides of lipopolysaccharides. Exemplary antigens of interest also include capsular organic polymers including those synthesized by microbes, e.g., bacteria, fungi, parasites, and viruses, and then purified from such a biological source using standard methods. Exemplary antigens of interest include microbial capsular organic polymers including those purified from bacterial organisms such as *Bacillus* species (including *B. anthracis*) (Wang and Lucas, *Infect. Immun.*, 72(9):5460-5463 (2004)), *Streptococcus pneumoniae* (Bentley et al., *PLoS Genet.*, 2(3):e31 (2006); Kolkman et al., *J. Biochemistry*, 123:937-945 (1998); and Kong et al., *J. Med. Microbiol.*, 54:351-356 (2005)), *Shigella* (Zhao et al., *Carbohydr. Res.*, 342(9):1275-1279 (2007)), *Haemophilus influenzae, Neisseria meningitidis, Staphylococcus aureus, Salmonella typhi, Streptococcus pyogenes, Escherichia coli* (Zhao et al., *Carbohydr. Res.*, 342(9):1275-1279 (2007)), and *Pseudomonas aeruginosa*, and fungal organisms such as *Cryptococcus* and *Candida*, as well as many other microorganisms (see, e.g., Ovodov, *Biochemistry (Mosc.)*, 71(9):937-954 (2006); Lee et al., Adv. Exp. Med. Biol., 491:453-471 (2001); and Lee, *Mol. Immunol.*, 24(10):1005-1019 (1987)). Exemplary antigens of interest also include polymers that do not occur in nature and thus are non-biological in origin.

Particular *Streptococcus pneumoniae* antigens include polysaccharide capsular type 1 (e.g., 1-g or 1-q), 2 (e.g., 2-g, 2-q, or 2-41A), 3 (e.g., 3-g, 3-q, 3-c, or 3-nz), 4, 5 (e.g., 5-q, 5-c, 5-qap, or 5-g), 6A (e.g., 6A-g, 6A-c1, 6A-c2, 6A-n, 6A-qap, 6A-6B-g, 6A-6B-q, or 6A-6B-s), 6B (e.g., 6B-c, 6A-6B-g, 6A-6B-q, or 6A-6B-s), 7F (e.g., 7F-7A), 7A (e.g., 7A-cn or 7F-7A), 7B (e.g., 7B-40), 7C (e.g., 7C-19C-24B), 8 (e.g., 8-g or 8-s), 9A (e.g., 9A-9V), 9L, 9N, 9V (e.g., 9A-9V), 9V and 14, 10F. (e.g., 10E-q, 10E-ca, or 10E-10C), 10A (e.g., 10A-17A or 10A-23F), 10B (e.g., 10B-10C), 11F, 11A (e.g., 11A-nz or 11A-11D-18F), 11B (e.g., 11B-11C), 11C (e.g., 11B-11C. or 11C-cn), 11D (e.g., 11A-11D-18F), 12F (e.g., 12F-q or 12F-12A-12B), 12A (e.g., 12A-cn, 12A-46, or 12F-12A-12B), 12B (e.g., 12F-12A-12B), 13

(e.g., 13-20), 14 (e.g., 14-g, 14-q, 14-v, or 14-c), 15F (e.g., 15F-cn1 or 15F-cn2), 15A (e.g., 15A-ca1, 15A-ca2, or 15A-chw), 15B (e.g., 15B-c, 15B-15C, 15B-15C-22F-22A), 15C (e.g., 15C-ca, 15C-q1, 15C-q2, 15C-q3, 15C-s, 15B-15C, or 15B-15C-22F-22A), 16F (e.g., 16F-q or 16F-nz), 16A, 17F (e.g., 17F-n and 17F-35B-35C-42), 17A (e.g., 17A-ca or 10A-17A), 18F (e.g., 18F-ca, 18F-w, or 11A-11D-18F), 18A (e.g., 18A-nz or 18A-q), 18B (e.g., 18B-18C), 18C (e.g., 18B-18C), 19F (e.g., 19F-g1, 19F-g2, 19F-g3, 19F-q, 19F-n, or 19F-c), 19A (e.g., 19A-g, 19A-, or 19A-ca), 19B, 19C (e.g., 19C-cn1, 19C-cn2, or 7C-19C-24B), (e.g., 13-20), 21 (e.g., 21-ca or 21-cn), 22F (e.g., 15B-15C-22F-22A), 23F (e.g., 23F-c, 10A-23F, or 23F-23A), 23B (e.g., 23B-c or 23B-q), 24F (e.g., 24F-cn1, 24F-cn2, or 24F-cn3), 24A, 24B (e.g., 7C-19C-24B), 25F (e.g., 25F-38), 25A, 27, 28F (e.g., 28F-28A or 28F-cn), 28A (e.g., 28F-28A), 29 (e.g., 29-ca or 29-q), 31, 32F (e.g., 32F-32A), 32A (e.g., 32A-cn or 32F-32A), 33F (e.g., 33F-g, 33F-q, 33F-chw, 33F-33B, or 33F-33A-35A), 33A (e.g., 33F-33A-35A), 33B (e.g., 33B-q, 33B-s, or 33F-33B), 33D, 34 (e.g., 34-ca or 34s), 35F (e.g., 35F-47F), 35A (e.g., 33F-33A-35A), 35B (e.g., 17F-35B-35C-42), 36, 37 (e.g., 37-g or 37-ca), 38 (e.g., 25F-38), 39 (e.g., 39-cn1 or 39-cn2), 40 (e.g., 7B-40), 41F (e.g., 41F-cn or 41F-s), 41A (e.g., 2-41A), 42 (e.g., 17B-35B-35C-42), 43, 44, 45, 46 (e.g., 46-s or 12A-46), 47F (e.g., 35F-47F), 47A, 48 (e.g., 48-cn1 or 48-cn2), or GenBank Accession Number AF532714 or AF532715.

Particular mention is made of *Streptococcus pneumoniae* polysaccharides selected from the group consisting of capsular type 3, 4, 6B, 7A, 7B, 7C, 7F, 9A, 9L, 9N, 9V, 12A, 12B, 12F, 14, 15A, 15B, 15C, 15F, 17, 18B, 18C, 19F, 23F, 25A, 25F, 33F, 35, 37, 38, 44, or 46.

Polycations

Desirably, any polycation which possesses a repetitive positive charge in the form of either a free primary, secondary or tertiary amine group may be used in the present invention. Exemplary polycations include but are not limited to poly-L-lysine, chitosan [β-(1-4)-linked copolymer of 2-amino-2-deoxy-β-D-glucan (GlcN) and 2-acetamido-2-deoxy-β-D-glucan (GlcNAc)], poly arginine and commercially available synthetic polymers that contain free amine groups such as branched polyethylenimine (PEI), Polyamine N7 (CAS 29320-38-5) and Ethylenediaminomethyl polystyrene (CAS 177987-93-8).

In desirable embodiments, the poly-L-lysine is α-poly-L-lysine (alpha-poly-L-lysine) or ε-poly-L-lysine (epsilon-poly-L-lysine). The lysine residues of poly-L-lysine are linked through a peptide bond between the carboxyl group and either the alpha (α-PLL) or epsilon (ε-PLL) amine group. Desirably the poly-L-lysine is α-poly-L-lysine. α-poly-L-lysine is chemically synthesized and can be obtained at various molecular weights, for example, 0.5 to 300KDa. ε-poly-L-lysine is small natural homopolymer of the essential amino acid L-lysine that is produced by bacterial fermentation, e.g., ε-poly-L-lysine can be isolated from *Streptomyces albus*, and has an average molecular mass of approximately 4000 Da.

The polycations are believed to perform two functions in the process of forming a matrix vaccine: 1) acting as a counterion to negatively charged antigen polymers and 2) in the case of primary amine containing polycations and crosslinkers that react with amine groups, aiding in the formation of the matrix by forming crosslinks with other polycation molecules or carrier protein molecules. Both of these properties of polycations will allow for improved entrapment of antigens in the protein matrix thereby improving the yield of PCMV particle formation. This can be observed in FIG. 1 where the amount of polysaccharides entrapped in the matrix improved from 5% to greater than 50% with the addition of αPLL.

Since formation of conjugate vaccines can also be negatively impacted by charge repulsion between the antigen and carrier protein, use of a polycation could also improve the efficiency of conjugation. Since many conjugation chemistries involve linking the polymer to the carrier protein via primary amine groups of the carrier protein (e.g., lysine residues), using a non-primary amine containing polycation such as poly arginine may be of benefit to avoid conjugation of the polymer antigen to the polycation. However, primary amine containing polycations could also be used to assist in making a matrix vaccine where the polysaccharides are intentionally covalently bound (crosslinked) to the matrix. The amount, size, and type of the polycation needed to improve antigen entrapment and matrix formation could depend on the composition, degree of negative charge, size, amine (or other reactive group) functionality, and secondary or tertiary structure of the polymeric antigen. In addition if more than one polymeric antigen is added to the matrix vaccine reaction (multivalent vaccine), the interactions between polymers could influence the polycation that is best at improving entrapment. This can be observed with the trivalent, 13-valent, and 23-valent PPS-PCMV experiments presented in Examples 5, 6, 8, and 9 below. When ϵ-PLL, which has an average molecular weight of 4000 Da, was used in the trivalent PCMV reactions, polysaccharide entrapment of PPS4, PPS18C, and PPS23F was modest and although improving immunogenicity of the polysaccharide antigens compared to the polysaccharide alone, they did not match the level observed with the conjugate vaccine. However, when ϵ-PLL was used in making the 13-valent PPS-PCMV the immunogenicity of PPS4 and PPS18C improved 3.4-fold and 107-fold, respectively, compared to the trivalent PPS-PCMV, suggesting that entrapment of these two polysaccharides was improved by ϵ-PLL due to interactions with the other polysaccharides in the 13-valent PPS reaction. Use of α-PLL (150-300 kDa) in the trivalent reactions improved the immunogenicity of PPS4 even further, eliciting a GMT that was 132-fold higher than that elicited by the 13-valent PPS PCMV. However, use of α-PLL (150-300 kDa) in making the 23-valent PPS-PCMV seemed to result in less PPS4 entrapment, as the GMT for PPS4 in this PCMV was 2650-fold less than the trivalent PPS/α-PLL PCMV, suggesting that the other polysaccharides in the 23-valent reaction may have a negative impact on the entrapment of PPS4 with α-PLL (150-300 kDa). Determining the optimal amount, size (molecular weight), and composition of the polycation component used to entrap each individual or group of polysaccharides or other antigens may be determined empirically by examining the ability of the polycation to cause the polysaccharide antigen(s) to shift to a higher molecular weight as determined by size exclusion chromatography. This shift, indicating the association of the antigens with larger sized particles as the antigen is entrapped and associated with a protein matrix, can be observed in several of the figures presented herein and discussed below.

Vaccine Compositions

The vaccine compositions of the invention, including PCMVs, may be used in combination, for example, in pediatric vaccines. In addition, the vaccine compositions of the invention may be used to vaccinate against, for example, pneumococcal infection, *Haemophilus influenzae* type B ("HiB") infection, *Streptococcus*(groups A and B)infection, meningococcal(e.g., *Neisseria meningitides*)infection, and may be used as capsular and O antigen vaccines against Gram negative bacteria (e.g., *Pseudomonas aeruginosa, Francisella tularensis, Shigella* species, *Salmonella* enteric serovars, *Acinetobacter* species, *Burkholderia*species, and *Escherichia coli*).

The vaccine formulation desirably includes at least one carrier protein, one or more antigen of interest, at least one polycation, and a pharmaceutically acceptable carrier or excipient (e.g., aluminum phosphate, sodium chloride, sterile water). A vaccine composition may also include an adjuvant system for enhancing the immunogenicity of the formulation, such as oil in a water system, alum, or other systems known in the art or other pharmaceutically acceptable excipients. An antigen/carrier protein/polycation matrix complex that is insoluble under physiological conditions is desirable to slowly release the antigen after administration to a subject. Such a complex desirably is delivered in a suspension containing pharmaceutically acceptable excipients. However, the antigen/carrier protein/polycation matrix complex may also be soluble under physiological conditions.

Typically the protein matrix vaccine composition is in a volume of about 0.5 ml for subcutaneous injection, 0.5 ml for intramuscular injection, 0.1 ml for intradermal injection, or 0.002-0.02 ml for percutaneous administration. A 0.5 ml dose of the protein matrix vaccine composition may contain approximately 2-500 µg of the antigen entrapped with approximately 2-500 µg of the carrier protein/polycation matrix. In a desirable embodiment, in a 0.5 ml dose, approximately 10 µg of the antigen are entrapped with approximately 10 µg of the carrier protein/polycation matrix. The molar ratio of antigen to carrier protein/polycation desirably is between 1 to 10 (e.g., 1 part antigen to 2 parts carrier/polycation or 1 part antigen to 3 parts carrier/polycation, etc., up to 1 part antigen to 10 parts carrier/polycation) and 10 to 1 (e.g., 10 parts antigen to 1 part carrier/polycation or 9 parts antigen to 1 part carrier/polycation, etc.). In a desirable embodiment, the molar ratio of antigen to carrier/polycation is 1 to 1. Alternatively, the ratio by dry weight of antigen to carrier protein/polycation desirably is between 1 to 10 and 10 to 1 (e.g., 1 to 1 by dry weight).

Because the antigen/carrier protein/polycation matrix complex may be degraded in the stomach, the vaccine composition is desirably administered parenterally (for instance, by subcutaneous, intramuscular, intravenous, intraperitoneal, or intradermal injection). While delivery by a means that physically penetrates the dermal layer is desirable (e.g., a needle, airgun, or abrasion), the vaccine compositions of the invention can also be administered by transdermal absorption.

In particular, the vaccine compositions of the invention may be administered to a subject, e.g., by intramuscular injection, intradermal injection, or transcutaneous immunization with appropriate immune adjuvants. Vaccine compositions of the invention may be administered one or more times, often including a second administration designed to boost production of antibodies in a subject, to prevent infection by an infectious agent corresponding to the antigen(s) included in the vaccine. The frequency and quantity of vaccine dosage to obtain the desired immune response or level of immunity depends on the specific activity of the vaccine and can be readily determined by routine experimentation. For example, for an infant, a vaccine schedule may be three doses of 0.5 ml each at approximately four- to eight-week intervals (starting at two months of age) followed by a fourth dose of 0.5 ml at approximately twelve to fifteen months of age. A fifth dose between four and six years of age may be desirable for some vaccines.

While the age at which the first dosage is administered generally is two months, a vaccine may be administered to infants as young as 6 weeks of age. For adults, two or more 0.5 ml doses given at intervals of 2-8 weeks generally are sufficient to provide long-term protection. A booster dose is desirably given every ten years to previously immunized adults and children above eleven years of age.

The vaccine compositions of the present invention may be presented in unit-dose or multi-dose containers, for example, sealed ampoules and vials and may be stored in a freeze-dried (lyophilized) condition requiring only the addition of the sterile liquid carrier immediately prior to use. Vaccines of the invention can be formulated in pharmacologically acceptable vehicles, e.g., alum hydroxide gel, adjuvant preparation, or saline, and then administered, e.g., by intramuscular injection, intradermal injection, or transcutaneous immunization with appropriate immune adjuvants.

The invention also includes kits that include a vaccine described herein (e.g., a PCMV). The kits of the invention can also include instructions for using the kits in the vaccination methods described herein.

The efficacy of the immunization schedule may be determined by using standard methods for measuring the antibody titer in the immunized subject. In general, mean antibody titers (desirably IgG titers) of approximately 1 µg/ml are considered indicative of long-term protection.

The invention provides vaccine compositions containing an antigen of interest entrapped with a carrier protein/polycation matrix, methods of making such vaccine compositions, and methods of vaccine administration. It has been discovered that the efficiency of PCMV formation and hence their cost effectiveness as vaccines, is improved by the addition of a polycation, e.g., poly-L-lysine, to the protein matrix. In addition, polycations may also be beneficial in improving the efficiency of conjugation reactions for the production of conventional conjugate vaccines, where the polymer antigen is covalently bound to the carrier protein, thus making a more cost effective conjugate vaccine. Briefly, as taught herein, protein matrix vaccine compositions which incorporate a polycation have increased immunogenicity compared to compositions comprised of antigen alone or antigen entrapped in a carrier protein matrix that does not contain polycation. The improved immunogenicity in protein matrix vaccine compositions containing polycation is believed to be due to improved entrapment of the polysaccharide antigen in the protein/polycation matrix, allowing for a higher level of antigen in a vaccine dose compared to the same dose of a vaccine that did not contain polycation. As discussed herein, polysaccharide capsules of bacteria are composed of repeating sugars and for many pathogenic bacteria these capsules carry a net negative charge. The negative charge of the capsule may be repelling the matrix protein, resulting in poor polysaccharide antigen entrapment. To counteract this negative charge a polycation, for example, poly-L-lysine (PLL), can be added to PCMV reactions. In addition primary amine containing polycations like PLL, can also aid in matrix formation by forming crosslinks between other PLL molecules or carrier protein molecules.

While the examples below depict embodiments utilizing polycations in the formation of protein matrix vaccines, the beneficial use of polycations can be similarly utilized in the production of conventional conjugate vaccines as well.

The invention is described below by reference to specific examples, embodiments and figures, the purpose of which is to illustrate the invention rather than to limit its scope. The following examples are not to be construed as limiting.

EXAMPLE 1

Vi-CRM197-αPLL PCMV

The effect of the addition of polycations in matrix vaccine compositions was investigated using Vi polysaccharide capsule from *Salmonella enterica* Serovar Typhi as an antigen, using a nontoxic diphtheria toxin CRM 197 as a carrier protein (prepared at Matrivax Research and Development Corporation, Boston, Mass., USA), and α-poly-L-lysine (Sigma-Aldrich, St. Louis, Mo.) as the polycation.

Vi is a highly anionic homoploymer composed of (α1-4)-D-GalANAc variably O-acetylated at C-3. One of the current approved vaccines for typhoid fever is TyphimVi® (Sanofi Pasteur SA), which contains unconjugated Vi polysaccharide as the antigen. In initial studies to test whether protein matrix vaccines could successfully be used to deliver Vi antigen and elicit an immune response, PCMVs were prepared in reactions containing 4 mg/mL Vi as the antigen and 4 mg/mL CRM197 as the matrix-forming carrier protein. Matrix formation was initiated by the addition of glutaraldehyde as the crosslinking agent. After incubation for 24 hr at 4° C. with constant rocking, the reaction was separated on a 2.6×10 cm column of Sepharose CL2B and high molecular weight fractions were collected, adjuvanted with alum, and used to immunize mice. Using the amount of Vi that shifted to a higher molecular weight following reaction it was estimated that <5% of the Vi in the PCMV reaction was entrapped in the protein matrix. Anti-Vi antibody titers for the PCMV compositions were approximately 3-fold higher than the polysaccharide alone (control), yet were lower than those elicited by the current commercial Vi polysaccharide vaccine TyphimVi®. In contrast, Vi conjugate vaccines, e.g., Vi-CRM197, have been shown in the literature to elicit titers that were 40-100 fold higher than the polysaccharide alone. See, e.g., Rondini et al., 2011, *Clinical and Vaccine Immunology*, 18: 460-468; Cui et al., 2010, *Clinical and Vaccine Immunology*, 17: 73-79; An et al. 2011 Vaccine 44: 7618-7623 Micoli et al., 2011, *Vaccine*, 29:712-720.

The poor immunogenicity of Vi PCMV particles compared to the conjugate vaccines was thought to be potentially due to poor entrapment of the Vi in the CRM197 matrix, poor separation of PCMV particles from non-entrapped (free) Vi, or both.

Due to the high anionic nature of Vi, it was hypothesized that Vi is repelling the CRM197 during the key cross-linking step and interfering with efficient entrapment into PCMV particles.

Initially, the addition of salt to the PCMV was investigated to reduce charge repulsion; however, an insoluble precipitate formed following crosslinking.

Figure 2:
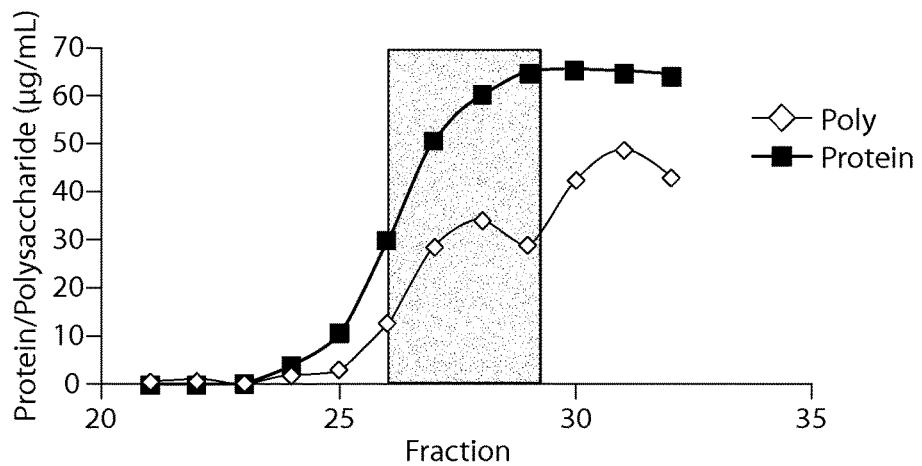
FIG. 2 is a graph showing the separation of a Vi-CRM197-αPLL (150-300 kDa) PCMV by size exclusion chromatography. The PCMV reaction was separated on a 150 mL (30 cm×2.6 cm) Sephacryl S-100 column. The amount of Vi polysaccharide and protein in the fractions was determined using the Stains-all assay and microBCA assay, respectively. Shaded box indicates fractions that were pooled and used for immunization of mice in preclinical trial.

The effect of a polycation was investigated on the PCMV process: Two PCMVs were prepared for the first immunization experiment using poly-L-lysine (PLL), each PCMV reaction contained 4 mg/ml Vi, 4 mg/ml CRM197 and 0.01% α-poly-L-lysine (150-300 kDa). Vi and α-poly-L-lysine (α-PLL) were incubated for 15 minutes at room temperature with continuous rocking before addition of 0.25% glutaraldehyde as crosslinking agent and CRM197 as the carrier protein. 0.01 mg/mL flagellin (Flg) from *Salmonella enterica* serovar Typhimurium was added to one of the reaction mixtures as an adjuvanting additive. Incubation was continued for an additional 10 minutes at room temperature with continuous rocking before being placed at 4° C. for 24 hours with constant rocking. Separation of the PCMV reactions was carried out on a 2.6×30 cm Sephacryl S-1000. Following separation of the reaction products on column, protein and polysaccharide levels were determined using microBCA (Pierce Chemical) and Stains-All (Sigma Chemical) assay kits, respectively. Approximately 20% of the Vi was shifted to a higher molecular weight and co-eluted with the peak of protein, suggesting that the Vi was entrapped within the carrier protein/polycation matrix (FIG. 2). These high molecular weight fractions were collected and pooled (see, FIG. 2, boxed fractions), alum adjuvanted, and used for immunization.

Groups of five Ba1BC mice (Jackson Laboratories) were immunized with 10 μg of Vi in the form of PCMV, Matrivax Vi alone, or TyphimVi® typhoid Vi polysaccharide vaccine (Sanofi Pasteur SA) at 3 biweekly intervals. Mice were sacrificed 3 weeks after their last immunization and the level of Vi-specific antibodies determined by ELISA assays. The endpoint geometric mean titers (GMTs) from the above immunizations are shown in Table 1.

TABLE 1

Immunogenicity of Vi-CRM197 PCMVs made with αPLL

| Groups (dosed by μg Vi) | Anti-Vi IgG GMT |
|---|---|
| 10 μg Vi-CRM197-αPLL PCMV + Alum | 65,302 |
| 10 μg Vi-CRM197-αPLL-Flg PCMV + Alum | 492,092 |
| Vi | 1,600 |
| Typhim Vi ® | 5572 |

From these results it can be seen that by using α-PLL in reactions, the PCMVs elicited anti-Vi antibody titers that were 40-fold higher than those observed with Vi polysaccharide alone (Table 1,). In addition, incorporation of small amounts of flagellin in the α-PLL-containing PCMV led to even higher anti-Vi antibody titers with a GMT that was 300-fold greater than immunization with the Vi polysaccharide alone and 7.5-fold greater than the PCMV without flagellin. The presence of the flagellin did not affect the amount of Vi entrapped by PLL (data not shown).

Interestingly, poly-L-arginine (PLA), which is also a polycation and contains the same degree of positive charge as PLL, but which does not contain repeating primary amines, did not improve Vi entrapment (data not shown), indicating that PLL was both counteracting the negative charge of the Vi as well as aiding in matrix formation by cross-linking to other PLL molecules and CRM197.

EXAMPLE 2

Improved Separation of Vi-CRM197-αPLL PCMVs

Figure 3:
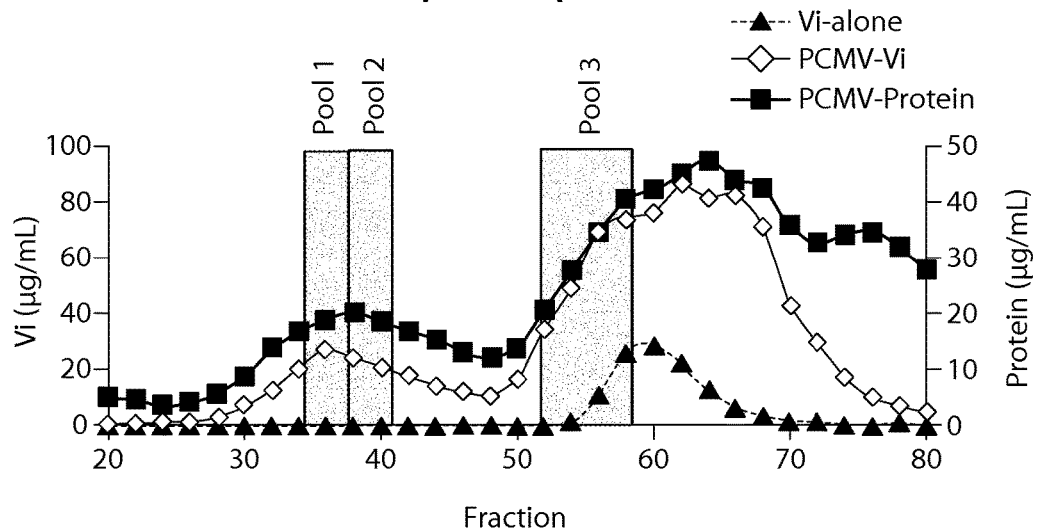
FIG. 3 is a graph showing the separation of Vi-CRM197-αPLL (150-300 kDa) PCMV by size exclusion chromatography. The PCMV reaction was separated on a 500 mL (90 cm×2.6 cm) Sephacryl S-1000 column. The amount of Vi polysaccharide and protein in the fractions was determined using the Stains-all assay and microBCA assay, respectively. Shaded boxes indicate fractions that were pooled and used for immunization of mice in preclinical trial.

In order to better eliminate low molecular weight species (assumed to be non-entrapped, unconjugated antigen polymer) from the PCMV particles, a longer (90 cm) size exclusion column was used. Specifically, a PCMV cross-linking reaction mixture containing 4 mg/ml Vi, 4 mg/ml CRM197 and 0.01% α-poly-L-lysine (150-300 KDa) was prepared. Vi and αPLL were incubated for 15 minutes at room temperature with continuous rocking before the addition of 0.25% glutaraldehyde and CRM197. Incubation was continued for an additional 10 minutes at room temperature with continuous rocking followed by incubation for 24 hr at 4° C. with constant rocking. Following separation of the reaction product on the SEC column, protein and polysaccharide levels were determined using microBCA and stains-all assay, respectively. To determine if the size or molecular weight of PCMV particles affect their immunogenicity, fractions from 3 different elution points from the SEC column were pooled and used for immunization. The pool selections are illustrated in FIG. 3. Pool 1 and pool 2 did not differ significantly in their elution from the column, however, pool 3 was suspected to have a lower molecular weight than pools 1 and 2 and to contain more non-entrapped Vi.

Groups of five mice were immunized with 10 μg of Vi from the subject compositions via 3 biweekly injections. Mice were sacrificed 3 weeks after their last immunization and the level of Vi-specific antibodies determined by ELISA assays. The endpoint GMTs from the above immunizations were compared (Table 2).

The combination of PLL and improved size separation allowed us to make a Vi-CRM197 PCMVs that elicited anti-Vi antibody titers that were 485-fold to 1400-fold higher than Vi alone and 22-fold higher than TyphimVi® typhoid vaccine (Table 2; pool 1 and 2).

TABLE 2

Immunogenicity of different size fractions of a Vi-CRM197-αPLL PCMV

| Groups (dosed by μg Vi) | Anti-Vi IgG GMT |
|---|---|
| 10 μg Vi-CRM197-αPLL PCMV (pool 1) + alum | 11,652 |
| 10 μg Vi-CRM197-αPLL PCMV (pool 2) + alum | 33,779 |
| 10 μg Vi-CRM197-αPLL PCMV (pool 3) + alum | 1,063 |
| 10 μg Vi alone | 24 |
| Naïve | 5 |

Although the GMT for PCMV from pool 3 was 44-fold higher than Vi alone and 1.3-fold higher than the commercial TyphimVi® typhoid vaccine, it was lower than those elicited by pool 1 and 2. This is likely due to the lower molecular weight of the PCMVs and/or the presence of higher amounts of unentrapped, or "free", Vi.

EXAMPLE 3

PPS18C-CRM197-αPLL PCMV

Figure 4:
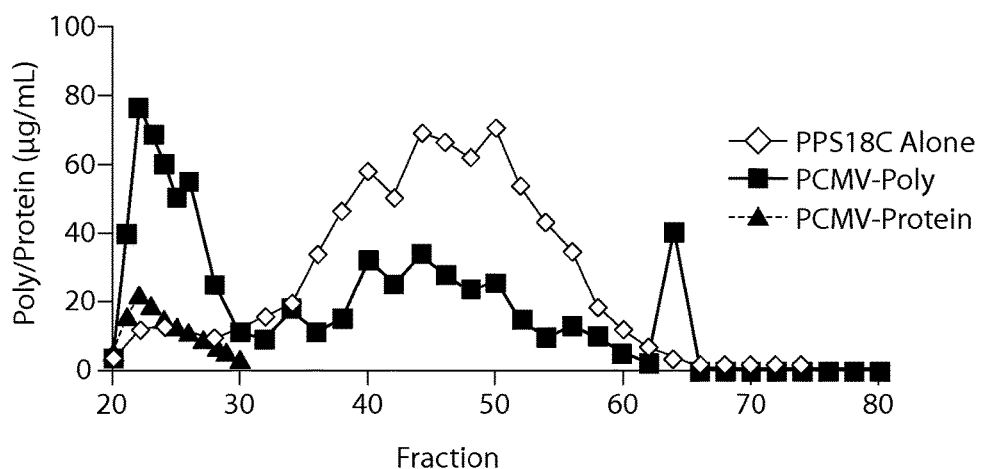
FIG. 4 is a graph showing the separation of pneumococcal polysaccharide 18C (PPS18C) and a PPS18C-CRM197-αPLL(15-30 kDa)-PCMV by size exclusion chromatography. PPS18C and a PPS18C-CRM197-αPLL-PCMV were separated on a 500 mL (90cm x 2.6 cm) Sephacryl S-1000 column. The amount of polysaccharide in the fractions was determined using Anthrone assay and the amount of protein determined using microBCA protein assay.

With the improvement in Vi entrapment using α-PLL, we next tested whether α-PLL would improve entrapment of the less negatively charged pneumococcal polysaccharide PPS 18C. Unlike Vi, where every sugar residue is negatively charged, PPS 18C has only a single negative charge for every 5 sugar residues. However, inclusion of 0.04% α-PLL (15-30 kDa) in the PCMV reactions resulted in a shift of 35% of the polysaccharide from a lower molecular weight to a higher molecular weight fraction when separated by SEC (FIG. 4). The majority of the CRM197 present in the PCMV reaction also co-localized to the high molecular weight fractions. The polysaccharide present in the high molecular weight fractions was shown to be captured in a PCMV particle by using a capture ELISA assay where the PCMV particles are bound to the ELISA plate via anti-CRM 197 antibodies and the polysaccharide detected using serotype specific antisera (data not shown).

EXAMPLE 4

Increased PLL Increases Vi Entrapment in PCMV

Figure 5:
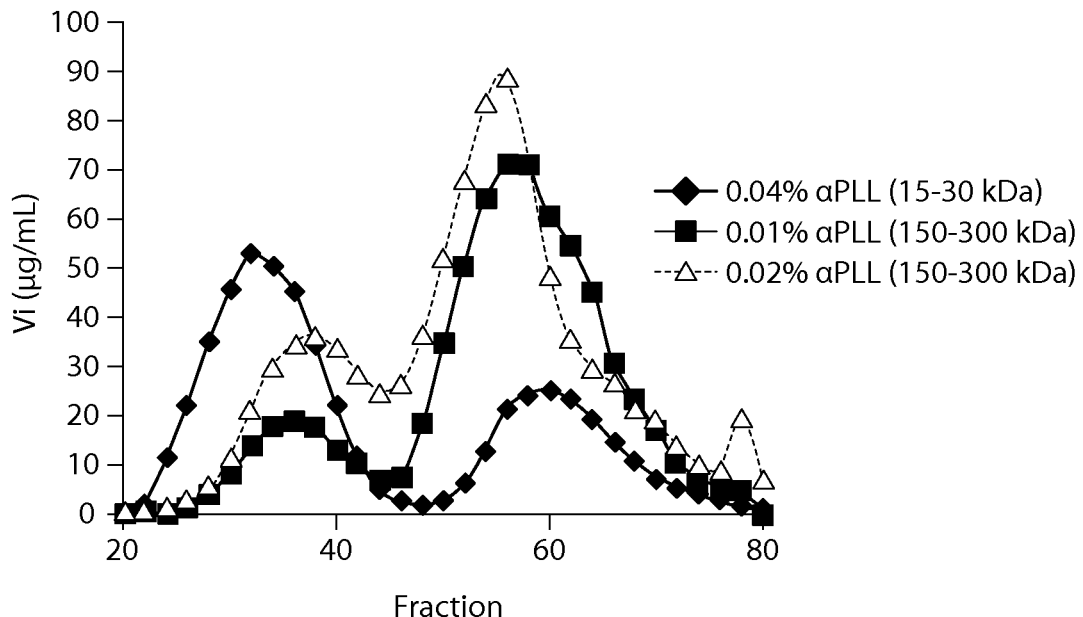
FIG. 5 is a graph showing the increase in the amount of entrapped Vi with increasing αPLL amount. 4 mg/mL Vi was added to PCMV reactions containing 0.01% aPLL (150-300 kDa), 0.02% αPLL (150-300 kDa), or 0.04% αPLL (15-30 kDa). After addition of glutaraldehyde and CRM197, reactions were separated on a 500 mL (90 cm×2.6 cm) Sephacryl S-1000 size exclusion column. Fractions were analyzed for polysaccharide and protein using the Stains-all assay and microBCA assay, respectively.

PCMV crosslinking reactions were performed using 0.01% and 0.02% of αPLL (150-300 kDa) and 0.04% αPLL (15-30 kDa), 4 mg/mL Vi and 4 mg/mL CRM197. Reactions were separated on a 500 mL (90 cm×2.6 cm) Sepharcryl S-1000 column and fractions analyzed for protein and polysaccharide using microBCA and Stains-all assay, respectively (FIG. 5). By increasing PLL (150-300 kDa) concentration from 0.01% to 0.02% the amount of entrapped Vi increased from 15% to 21%. The increased Vi entrapment had no effect on the immunogenicity of the PCMV with PCMVs synthesized using both concentrations of PLL eliciting anti-Vi antibody titers that were 14- to 20-fold higher than Vi alone and 2- to 3-fold higher than TyphimVi® typhoid vaccine (data not shown). When 0.04% of a smaller α-PLL (15-30 kDa) was utilized the amount of entrapped Vi increased to 64%. The increased entrapment with the lower molecular weight PLL did not result in improved immunogenicity of the PCMV over the Vi alone (data not shown). We have hypothesized that the higher concentration of the lower molecular weight α-PLL (15-30 kDa) may be masking Vi epitopes (data not shown).

EXAMPLE 5

Trivalent PCMV

Figure 6:
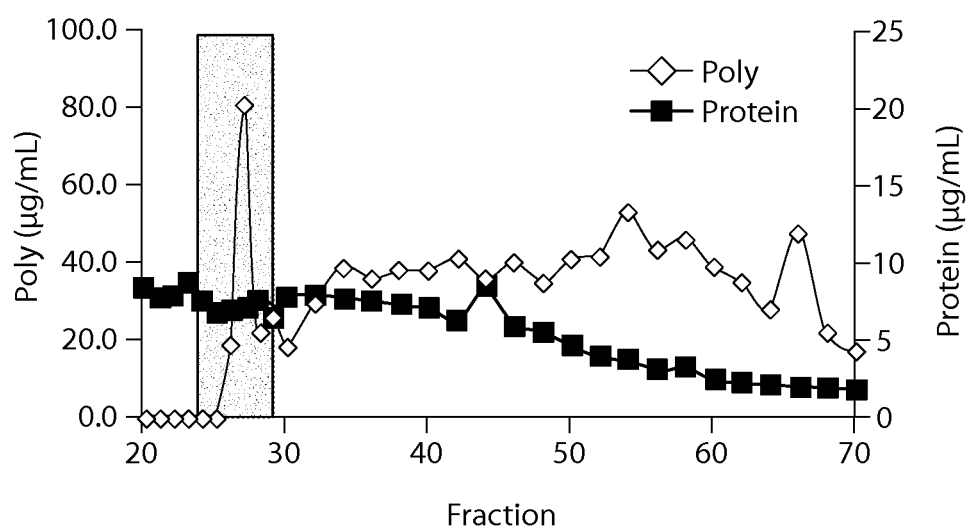
FIG. 6 is a graph showing the separation of a batched trivalent PPS (PPS4, PPS 18C, PPS23F)-CRM197-εPLL PCMV by size exclusion chromatography. Three pneumococcal polysaccharides (1.3 mg/mL each of PPS4, PPS 18C, and PPS23F) were added to a single PCMV reaction. The reaction was separated on a 500 mL (90 cm×2.6 cm) Sephacryl S-1000 column. Column fractions were analyzed for total polysaccharide and protein using the Anthrone assay and microBCA, respectively. The shaded box indicates the fractions that were pooled for immunization of mice in a preclinical immunogenicity trial.

To investigate whether the beneficial effects of a polycation to a PCMV could be used in multivalent PCMVs, a trivalent pneumococcal vaccine incorporating pneumococcal polysaccharide antigens PPS18C, PPS4, and PPS23F was prepared. The PCMV was prepared as follows: The PCMV reaction mixture contained 5 mg/ml total polysaccharide (roughly 1.7 mg/ml each of PPS18C, PPS4, and PPS23F), 1 mg/ml CRM197 and 0.04% ε-poly-L-lysine (4 kDa, Bainafo Bioengineering Co. Ltd., Zhengzhou, PRC). Polysaccharide and ε-poly-L-lysine was incubated for 15 minutes at room temperature with continuous rocking before addition of 0.25% glutaraldehyde as crosslinking agent and CRM197 as the matrix protein. Incubation was continued for an additional 10 minutes at room temperature with continuous rocking before being placed at 4° C. for 24 hours with constant rocking. Separation of the PPS18C/PPS4/PPS23-CRM197-εPLL PCMV was carried out on a 2.6×90 cm Sepharcryl S-1000 column. Fractions were analyzed for polysaccharide using the anthrone assay, for protein by MicroBCA, and for entrapment of each polysaccharide in PCMV particles by using a capture ELISA (see FIG. 5). The anthrone assay is a colorometic assay for the detection of hexoses following hydrolysis in concentrated sulfuric acid. Trevelyan, et al., 1952, "Determination of Yeast Carbohydrates with the Anthrone Reagent", *Nature*, 170(4328): 626-627. A strong positive capture ELISA was observed for PPS4 (data not shown); however, weak signals were observed with PPS18C and 23F. Fractions containing high molecular weight polysaccharide that were positive in the capture ELISA were pooled (see, FIG. 6, boxed fractions), alum adjuvanted, and used for immunizations.

Groups of 10 mice were immunized using the same dosing regimen as described above for Vi-PCMVs. For the trivalent batched PCMVs, each dose contained 2 μg each PS or 6 μg total polysaccharide. Prevnar®13 conjugate vaccine (which contains 2.2 μg of each PS per dose except for 6B, which is at 4 μg for a total of 30.8 μg PPS) was administered to a group of mice as a positive control for comparison with the PCMV-induced antibody responses. A group of mice was also immunized with the antigens alone, i.e., the thirteen unconjugated polysaccharide antigens found in the 13-valent Prevnar®13, at 2 μg of each polysaccharide for a total of 26 μg of total polysaccharide per dose. A group of naïve (unvaccinated) mice was also included as a negative control group.

At about 2.5 weeks (day 47) after the third immunization, all mice were euthanized and blood collected by cardiac puncture. The immune sera were analyzed by PPS-specific ELISAs for antigen-specific IgG antibody responses recognizing PPS4, PPS18C, and PPS23. Anti-PPS IgG geometric mean antibody titers (GMT) were calculated from the titers from individual sera from immunized animals. Results are show in Table 3 below.

TABLE 3

Trivalent PPS18C/PPS4/PPS23-CRM197-ePLL PCMV antibody titers

| Groups (μg total PPS per dose) | Anti-PPS4 IgG GMT | Anti-PPS18C IgG GMT | Anti-PPS23F IgG GMT |
|---|---|---|---|
| 6 μg Batched Trivalent PPS-CRM197-ePLL PCMV + alum | 1974 | 905 | 905 |
| 26 μg of 13 PPS (polysaccharides alone) | 11 | 31 | 17 |
| Prevnar ®13 | 73517 | 7563 | 2560 |
| Naïve | 11 | 10 | 10 |

As can be seen in Table 3, the batched PCMV containing ε-PLL elicited an anti-PPS4 GMT that was 179-fold higher than polysaccharide alone, an anti-PPS18C GMT that was 29-fold higher than polysaccharide alone, and an anti-PPS23F GMT that was 53-fold higher than polysaccharide alone. These GMTs were 37-fold lower, 8.3-fold lower, and 2.8-fold lower than the GMT of the Prevnar®13 conjugate vaccine for PPS4, PPS18C, and PPS23F, respectively. Although the titers elicited from the batched trivalent PCMV were not as high as those elicited by the Prevnar®13 conjugate vaccine, they represented a dramatic improvement over the use of antigen alone and over previous pneumococcal polysaccharide PCMVs made without PLL and using DNI as the matrix protein. This study demonstrates the feasibility of using polycation addition in PCMV formation to improve immunogenicity of multivalent vaccines as well as monovalent vaccines. In addition, the ease of multivalent vaccine production using PCMV technology as compared with conventional conjugate vaccine production is clearly advantageous.

EXAMPLE 6

Batched 13-Valent Pneumococcal Polysaccharide PCMV

A 13-valent pneumococcal vaccine incorporating the pneumococcal polysaccharide antigens currently included in Prevnar®13 conjugate vaccine, i.e., PPS1, PPS3, PPS4, PPS5, PPS6A, PPS6B, PPS7F, PPS9V, PPS14, PPS18C, PPS19A, PPS19F and PPS23F, was prepared and tested to further investigate the beneficial effects of polycation addition to PCMV matrix-forming reaction mixes.

Figure 7:
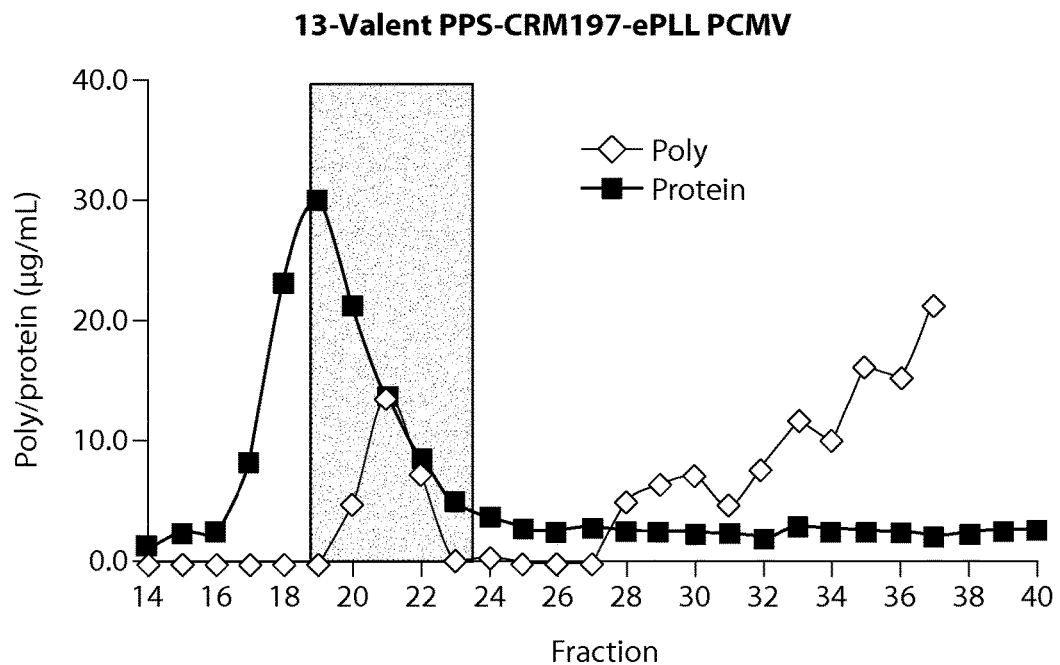
FIG. 7 is a graph showing the separation of a batched 13-valent PPS-CRM197-αPLL (150-300 kDa) PCMV by size exclusion chromatography. The 13 pneumococcal polysaccharides present in Prevnar® 13 conjugate vaccine were added to a single PCMV reaction (0.3 mg/mL of each polysaccharide). The reaction was separated on a 500 mL (90 cm×2.6 cm) Sephacryl S-1000 column. Column fractions were analyzed for total polysaccharide and protein using the Anthrone assay and microBCA, respectively. The shaded box indicates the fractions that were pooled for immunization of mice in a preclinical immunogenicity trial.

The PCMV was prepared as follows: a PCMV reaction mixture contained 4 mg/ml total polysaccharide (roughly 0.3 mg/ml each of each polysaccharide antigen), 4 mg/ml CRM197 and 0.4 mg/ml ε-poly-L-lysine (4 kDa, Bainafo Bioengineering Co. Ltd., Zhengzhou, PRC). The polysaccharide and ε-poly-L-lysine were incubated for 15 minutes at room temperature with continuous rocking before addition of 0.25% glutaraldehyde as crosslinking agent and CRM197 as the matrix protein. Incubation was continued for an additional 10 minutes at room temperature with continuous rocking before being placed at 4° C. for 24 hours with constant rocking. Separation of the PPS-CRM197-ePLL PCMV was carried out on a 2.6×90 cm Sephacryl S-1000 column. Fractions were analyzed for polysaccharide using the anthrone assay, for protein by MicroBCA, and for entrapment of each polysaccharide in PCMV particles by capture ELISA. Fractions containing high molecular weight polysaccharide that were positive in the capture ELISA were pooled (see, FIG. 7, boxed fractions), alum adjuvanted, and used for immunizations.

Groups of 10 mice were immunized using the previously described dosing regimen at day 0, 14, and 28. For the 13-valent batched PCMV, each dose contained 4 μg of total polysaccharide. Prevnar®13 conjugate vaccine, which contains 2.2 μg of each polysaccharide per dose, except for 6B, which is at 4 μg for a total of 30.8 μg PPS, was administered to a group of mice as a positive control for comparison with PCMV-induced antibody responses. A group of mice was also immunized with the antigens alone, i.e., the thirteen unconjugated polysaccharide antigens found in the 13-valent Prevnar®13, at $2_{14}$ of each polysaccharide for a total of $26_{14}$ of total polysaccharide per dose. A group of naïve (unvaccinated) mice was also included as a negative control group.

At about 2.5 weeks (day 47) after the third immunization, all mice were euthanized and blood collected by cardiac puncture. The immune sera were analyzed by PPS-specific ELISA for antigen-specific IgG antibody responses to ten of the PPS antigens. Anti-PPS IgG geometric mean antibody titers (GMT) were calculated from the titers from individual sera from immunized animals. Results are show in Table 4.

TABLE 4

| 13-valent PPS-CRM197-ePLL PCMV antibody titers | | | | | | | | | | |
|---|---|---|---|---|---|---|---|---|---|---|
| Groups (μg TOTAL per dose) | Anti-PPS1 IgG GMT | Anti-PPS3 IgG GMT | Anti-PPS4 IgG GMT | Anti-PPS6B IgG GMT | Anti-PPS9V IgG GMT | Anti-PPS1 IgG GMT | Anti-PPS18C IgG GMT | Anti-PPS19A IgG GMT | Anti-PPS19F IgG GMT | Anti-PPS23F IgG GMT |
| 4 μg Batched 13-Valent (PPS-CRM197-ePLL) PCMV + Alum (~0.3 μg/PPS) | 121 | 5820 | 6686 | 557 | 1667 | 512000 | 97006 | 3200 | 222861 | 139 |

TABLE 4-continued 13-valent PPS-CRM197-ePLL PCMV antibody titers

| Groups (μg TOTAL per dose) | Anti-PPS1 IgG GMT | Anti-PPS3 IgG GMT | Anti-PPS4 IgG GMT | Anti-PPS6B IgG GMT | Anti-PPS9V IgG GMT | Anti-PPS1 IgG GMT | Anti-PPS18C IgG GMT | Anti-PPS19A IgG GMT | Anti-PPS19F IgG GMT | Anti-PPS23F IgG GMT |
|---|---|---|---|---|---|---|---|---|---|---|
| 26 μg cocktailed 13 PPS alone | 15 | 17 | 11 | 48 | 20 | 4935 | 31 | 86 | 226 | 17 |
| 30.8 μg Prevnar ® 13 vaccine (~2 μg/PPS) | 7760 | 11143 | 73517 | 970 | 134352 | 388023 | 7563 | 44110 | 33863 | 2560 |
| Naïve | 10 | 17 | 11 | 14 | 26 | 10 | 10 | 17 | 10 | 10 |

Endpoint IgG GMT from sera from mice immunized with batched PCMV formulations was dramatically higher than GMT from mice immunized with PPS alone (ranging from 8-fold to over 3.000-fold higher than PPS alone). From the data in Table 4 it can be seen that the batched 13-valent PCMV containing ε-PLL induced IgG GMT comparable to the GMT achieved by immunization with Prevnar®-13 (2 or 4 μg of each PPS), depending on the PPS antigen examined, using substantially less PPS antigen (~0.3 μg/PPS in PCMV vs. 2μg/4μg PPS in Prevnar®13).

From the immunological data from Table 3 and Table 4 above, it is clear that the tri- and 13-valent PCMVs containing ε-PLL demonstrate far more robust antibody immune responses than previous PCMVs that did not contain PLL or other polycation. Reformulation with higher reactant levels and size-fractionation of the PCMVs to remove unincorporated polysaccharide antigen(s) and matrix protein monomer, e.g., on a longer sizing column, improved the antigen-specific immune response above antigen alone. Also, inclusion of polycationic polymers α-PLL and/or ε-PLL increases entrapment efficiency of PS into the CRM-197-PCMV matrix and elicits a 3- to 125-fold more robust immune response compared to DNI-PCMV formulations that did not include α-PLL and ε-PLL (see example 7). As can be seen from the tables above, the antigen-specific antibody response induced by the PLL-formulated PCMVs is sometimes lower, comparable, or superior to the magnitude of the anti-PPS antigen immune responses achieved by Prevnar®13 conjugate vaccine; however, when it is noted that the PPS(13)-CRM197-EPLL PCMVs contain 0.3μg of each polysaccharide antigen per dose compared to the 2 μg or 4 μg of each PPS antigen in Prevnar®13 conjugate vaccine, it is appreciated that the PCMVs provide a uniquely efficient immunogenic composition and one that is also efficiently made in one reaction step (as compared to the multiplicity of separate conjugation reactions necessary for manufacture of the Prevnar®13 vaccine).

EXAMPLE 7

Cocktailed and Batched Bundled 13-Valent PPS-DNI PCMVs

A series of PCMVs was made using a non-toxic mutant form of protective antigen from B. anthracis (DNI) as the carrier protein. Thirteen separate PPS/DNI protein matrix vaccines were synthesized, each containing a different pneumococcal polysaccharide antigen (PPS) following the same crosslinking reaction procedure with 0.25% glutaraldehyde as described above. The PCMVs were then size separated on a 2.6×15 cm column of Sepharose CL2B. In addition, PCMV crosslinking reactions were performed that contained four polysaccharide antigens in the same PCMV reaction (batched antigens), to yield multivalent PCMVs. The multivalent PCMVs contained the following antigen "bundles":

Bundle 1: PPS3, PPS18C, PPS19F, PPS23F
Bundle 2: PPS4, PPS6A, PPS6B, PPS14
Bundle 3: PPS5, PPS7F, PPS9V, PPS19A PPS 1 was not included in the bundled PCMV reactions because it contains a primary amine in its repeating structure that can be covalently crosslinked to the carrier protein in the presence of glutaraldehyde. The batched-antigen PCMVs were then separated by SEC in the same manner as the monovalent PCMVs. The thirteen separate vaccine compositions were cocktailed to make the 13-valent cocktailed PPS-DNI—PCMV. The three batched-antigen PCMVs including the individual PPS 1-DNI PCMV were also cocktailed to make a batched bundled 13-valent PCMV. Groups of 10 mice were then immunized using either the cocktail of monovalent PCMVs or the cocktail of batched-antigen PCMVs. For the cocktailed monovalent PCMVs, mice were given either 2.2 μg or 6 μg of each polysaccharide. For the batched bundles, however, only 0.5 μg of each polysaccharide was delivered in each dose except for PPS1, where 2.2 μg was delivered. As controls, groups of mice were immunized with the 13 polysaccharides alone or the conjugate vaccine Prevnar®13. Each dose of Prevnar® contained 2 μg of each polysaccharide except PPS6B which is at 4 μg. Table 5 below presents a summary of the anti-PPS antibody titers from mice immunized with the cocktailed and batched bundled PCMVs.

TABLE 5

Anti-PPS antibody titers from Cocktailed 13-Valent PCMVs

| Groups (Dose given = μg EACH PPS) | Anti-PPS IgG GMT | | | | | |
|---|---|---|---|---|---|---|
| | 1 | 3 | 4 | 5 | 6A | 6B |
| 2.2 μg Cocktailed PCMV | 1140 | 94 | 98 | 79 | 251 | 127 |
| 2.2 μg Batched Bundles PCMV | 3318 | 106 | 90 | 198 | 396 | 280 |

TABLE 5-continued

Anti-PPS antibody titers from Cocktailed 13-Valent PCMVs

| | | | | | | |
|---|---|---|---|---|---|---|
| 2.2 µg 13-valent PPS only | 29 | 26 | 25 | 23 | 24 | 25 |
| 6 µg Cocktailed PCMV | 97 | 68 | 49 | 59 | 177 | 96 |
| 6 µg 13-valent PPS only | 24 | 28 | 25 | 32 | 37 | 25 |
| Prevnar-13 | 16225 | 15308 | 19096 | 804 | 4543 | 3708 |
| Naïve | 25 | 28 | 24 | 24 | 25 | 24 |

| Groups | Anti-PPS IgG GMT | | | | | | |
|---|---|---|---|---|---|---|---|
| (Dose given = µg EACH PPS) | 7F | 9V | 14 | 18C | 19A | 19F | 23F |
| 2.2 µg Cocktailed PCMV | 91 | 285 | 42759 | 207 | 1107 | 1678 | 134 |
| 2.2 µg Batched Bundles PCMV | 119 | 50 | 73069 | 512 | 1407 | 7258 | 357 |
| 2.2 µg 13-valent PPS only | 31 | 23 | 657 | 25 | 24 | 23 | 23 |
| 6 µg Cocktailed PCMV | 49 | 110 | 22696 | 209 | 229 | 441 | 64 |
| 6 µg 13-valent PPS only | 29 | 25 | 970 | 25 | 25 | 24 | 21 |
| Prevnar-13 | 11492 | 103612 | 171603 | 4789 | 25634 | 29182 | 766 |
| Naïve | 25 | 33 | 21 | 25 | 25 | 25 | 25 |

Both of the PCMV "cocktails" elicited polysaccharide antigen-specific titers that were above those elicited by the polysaccharide antigens alone, however, they were 2- to 200-fold less than the titers elicited by the Prevnar®13 conjugate vaccine (Pfizer Inc., USA). The results show that the bundling of batched-antigen PCMVs led to higher antibody titers for almost all antigens in comparison to immunization with the cocktailed monovalent PCMVs. The decreased immune response of the PCMV cocktails compared to Prevnar®13 was likely due to poor polysaccharide entrapment and separation of the PCMVs from the free polysaccharide, rather than to the amount of polysaccharide delivered per dose.

EXAMPLE 8

Trivalent Batched PPS-CRM197-αPLL PCMV and added Flagellin

Figure 8:
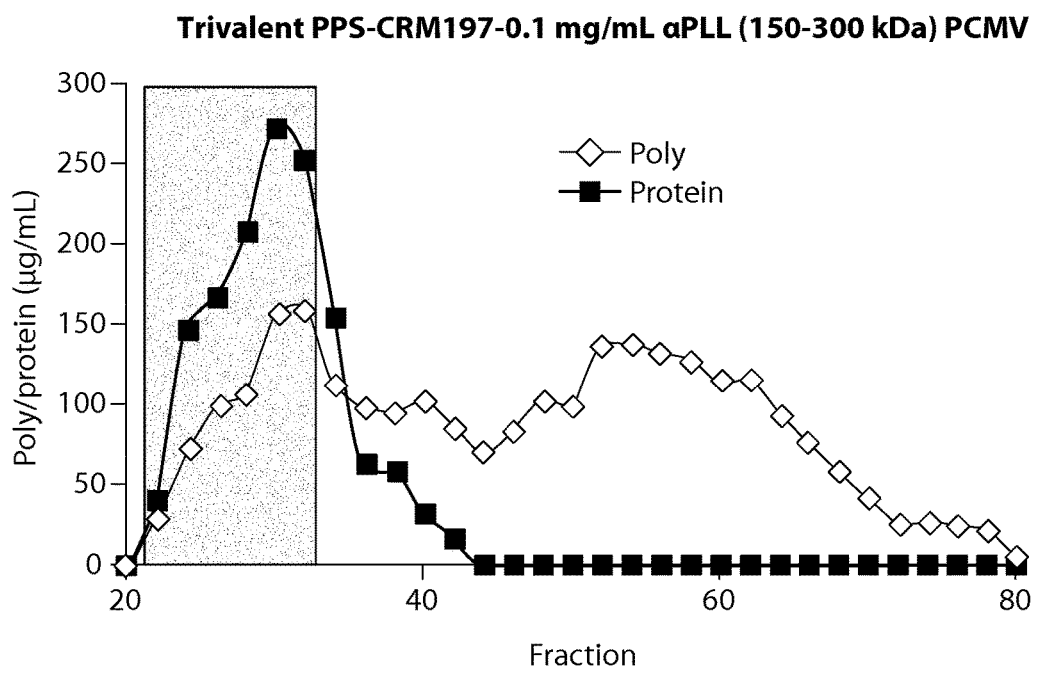
FIG. 8 is a graph showing the separation of a batched trivalent PPS (PPS4, PPS 18C, PPS23F)-CRM197-αPLL (150-300 kDa) PCMV by size exclusion chromatography. Three pneumococcal polysaccharides (1.3 mg/mL each of PPS4, PPS18C, and PPS23F) were added to a single PCMV reaction. The reaction was separated on a 500 mL (90 cm×2.6 cm) Sephacryl S-1000 column. Column fractions were analyzed for total polysaccharide and protein using the Anthrone assay and microBCA, respectively. The shaded box indicates the fractions that were pooled for immunization of mice in a preclinical immunogenicity trial.

A trivalent PCMV containing PPS4, 18C, and 23F pneumococcal polysaccharide antigens and CRM197 as a matrix-forming carrier protein and poly-L-lysine was made with and without flagellin. The PCMVs were prepared as follows: the PCMV reaction mixture contained 4 mg/ml total polysaccharide (1.33 mg/ml of each polysaccharide), 4 mg/ml CRM197 and 0.01% αPLL (150-300 kDa). The polysaccharides and αPLL were incubated for 15 minutes at room temperature with continuous rocking before addition of 0.25% glutaraldehyde. 0.001 mg/mL of flagellin from *Salmonella Typhimurium* (InvivoGen, San Diego, Calif., USA) were also added to one PCMV reaction mixture with the glutaraldehyde. Incubation was continued for an additional 30 minutes at room temperature with continuous rocking. The PCMV reaction products were separated on a 2.6×90 cm Sephacryl S-1000 column and the high molecular weight fractions were collected and pooled (see, FIG. 8, boxed fractions). Following separation of reaction on column, protein and polysaccharide levels were determined using microBCA and anthroneassay, respectively.

Groups of 10 mice were immunized as in previous examples using either the batched-antigen PCMV without flagellin or the batched-antigen PCMV with flagellin and used to immunize mice. Positive and negative controls were as in previous examples. Results are shown in Table 6.

TABLE 6

Anti-PPS antibody titers from bundled trivalent PPS-CRM197 PCMVs

| Groups (µg total PPS per dose, or ~2 µg each PPS) | Anti-PPS4 IgG GMT | Anti-PPS18C IgG GMT | Anti-PPS23F IgG GMT |
|---|---|---|---|
| 6 µg Batched Trivalent (PPS-CRM197-αPLL) PCMV + alum | 885,124 | 76,392 | 260 |
| 6 µg Batched Trivalent (PPS-CRM197-αPLL-Flagellin) PCMV + alum | 1,406,158 | 97,942 | 61 |
| 46 µg of Pneumovax ® (polysaccharides alone) | 15 | 25 | 19 |
| 30.8 µg Prevnar ®13 | 80,305 | 3,448 | 1,194 |
| Naïve | 15 | 10 | 13 |

In the PCMV that did not contain flagellin, the anti-PPS4 and PPS18 antibody titers were 59.000-fold and 3055-fold higher than polysaccharide alone and 11-fold and 22-fold higher than Prevnar®13, respectively, at a comparable dose (see, Table 7). The titers to PPS23F were marginally higher than polysaccharide alone and less than those elicited by Prevnar® suggesting that only low levels of PPS23F were entrapped in the PCMV particle. These data compared to the previous Trivalent PPS-CRM197-εPLL PCMV data (see Example 5) indicate that the use of the higher molecular weight αPLL as the polycation led to improved entrapment of antigen in the PCMV matrix and that judicious selection of antigens to be co-entrapped in the protein matrix, elimination of non-immunogenic species by, e.g., by size exclusion of low molecular weight components of the matrix-formation reaction product, judicious use of adjuvanting elements, e.g., flagellin, and judicious control of the amount of antigen entrapped and deliverable per dose provides PCMV vaccine compositions of comparable and even superior immunogenicity to the conjugate vaccine commercial products marketed today.

EXAMPLE 9

23-Valent PPS-CRM197 PCMVs

Figure 9:
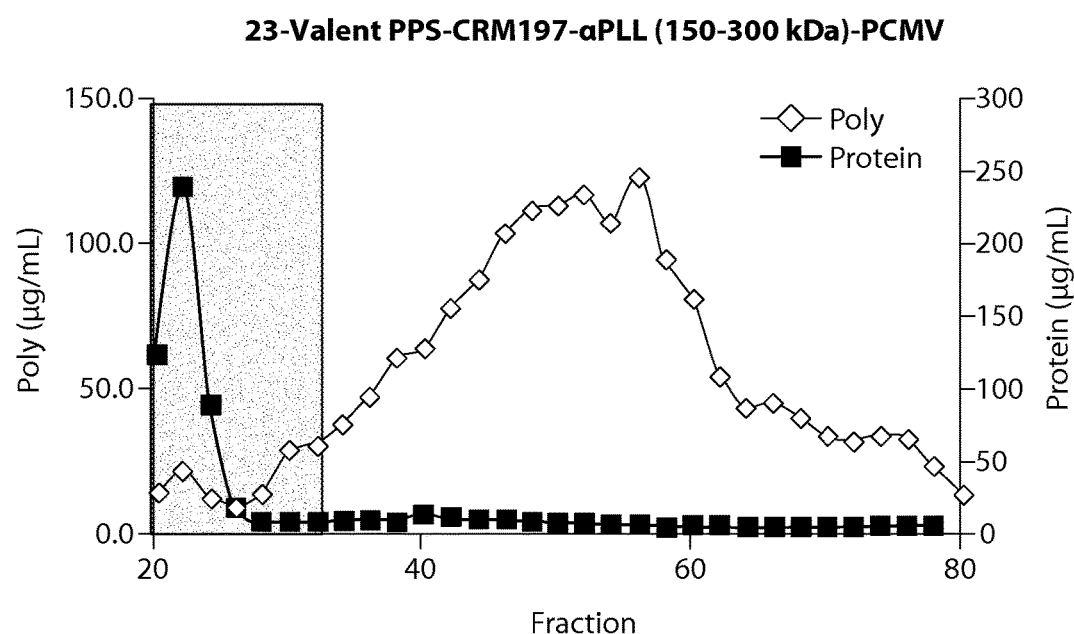
FIG. 9 is a graph showing the separation of a batched 23-valent PPS-CRM197-αPLL (150-300 kDa) PCMV by size exclusion chromatography. The 23 polysaccharides present in the polysaccharide only vaccine Pneumovax® were added to a single PCMV reaction (0.17 mg/mL of each polysaccharide). The reaction was separated on a 500 mL (90 cm×2.6 cm) Sephacryl S-1000 column. Column fractions were analyzed for total polysaccharide and protein using the Anthrone assay and microBCA, respectively. The shaded box indicates the fractions that were pooled for immunization of mice in a preclinical immunogenicity trial.

With the improvement in polysaccharide entrapment and immunogenicity observed by using α-PLL (150-300 kDa) in the Trivalent PPS-PCMV, a 23-valent PPS-PCMV was made using the 23 polysaccharides from the commercial vaccine Pneumovax®. After desalting and concentrating the 23 polysaccharides from Pneumovax® to 4 mg/mL (0.17 mg/mL of each polysaccharide), they were incubated with 0.01% α-PLL (150-300 kDa) for 15 minutes at room temperature with constant rocking. 0.25% glutaraldehyde was added along with 4 mg/mL CRM197 and incubation continued for 10 minutes at room temperature with constant rocking before being incubated for 24 hr at 4° C. with constant rocking. The PCMV reaction was separated on a 2.6 cm×90 cm column of Sephacryl S-1000 and the amount of total polysaccharide and protein in fractions determined using the anthrone assay and microBCA assay, respectively (FIG. 9). The high molecular weight fractions indicated by the box in FIG. 9 were pooled and used for immunizations.

Groups of 10 mice were immunized as in previous examples. Positive and negative controls were as in previous examples. Results are shown in Table 7.

TABLE 7

Anti-PPS GMTs from 23-Valent PPS-CRM197-αPLL (150-300 kDa) PCMV

| Groups (μg total PPS per dose, or ~0.26 μg each PPS) | Anti-PPS1 IgG GMT | Anti-PPS3 IgG GMT | Anti-PPS4 IgG GMT | Anti-PPS6B IgG GMT | Anti-PPS9V IgG GMT |
|---|---|---|---|---|---|
| 6 μg Batched 23 Valent (PPS-CRM197-α-PLL) PCMV + Alum | 1,731,183 | 106,649 | 334 | 735 | 59,714 |
| 6 μg of Pneumovax ® (polysaccharides alone) | 145 | 215 | 19 | 149 | 32 |
| 30.8 μg Prevnar®13 (~2 μg each PPS) | 22,286 | 146,269 | 80,305 | 4,159 | 362,039 |
| Naïve | 11 | 13 | 15 | 13 | 10 |

| Groups (μg total PPS per dose, or ~0.26 μg each PPS) | Anti-PPS14 IgG GMT | Anti-PPS18C IgG GMT | Anti-PPS19A IgG GMT | Anti-PPS19F IgG GMT | Anti-PPS23F IgG GMT |
|---|---|---|---|---|---|
| 6 μg Batched 23 Valent (PPS-CRM197-α-PLL) PCMV + Alum | 1,891,038 | 463,425 | 1,372 | 2,492 | 53 |
| 6 μg of Pneumovax ® (polysaccharides alone) | 1,030 | 70 | 26 | 61 | 70 |
| 30.8 μg Prevnar®13 (~2 μg each PPS) | 383,957 | 3,448 | 24,251 | 3,378 | 1,194 |
| Naïve | 17 | 10 | 17 | 16 | 13 |

The 23-valent PPS-PCMV elicited GMTs for PPS1, PPS14, and PPS18C that were 77-fold, 4.9-fold, and 134-fold higher than those elicited by the conjugate vaccine Prevnar®13, while the GMT for PPS3 and PPS 19F were equivalent to that elicited by Prevnar®13. In the 23-valent PCMV according to this invention, only 0.26 μg of each polysaccharide was delivered per dose while each dose of Prevnar®13 contains 2.2 μg of each polysaccharide (except PPB6B which is at 4 μg), indicating the 23-Valent PCMV was able to elicit higher titers than Prevnar®13 for several polysaccharides at a 7-fold lower dose. Although the GMTs for the other polysaccharides tested in this immunogenicity experiment were less than those elicited by Prevnar®13 they were still generally higher than the polysaccharide alone.

All patents, patent applications, patent application publications, and other publications cited or referred to herein are incorporated by reference to the same extent as if each independent patent, patent application, patent application publication or publication was specifically and individually indicated to be incorporated by reference.

We claim:

1. An immunogenic composition comprising (1) one or more antigen of interest, (2) one or more carrier protein, and (3) one or more polycation, wherein said carrier protein and said polycation are cross-linked to form a protein matrix, and said antigen of interest is entrapped by said protein matrix, wherein said immunogenic composition has increased immunogenicity compared to the antigen of interest alone and wherein said immunogenic composition has increased immunogenicity compared to a protein matrix vaccine composition including said antigen of interest but not incorporating said polycation.

2. The composition of claim 1, wherein said polycation is selected from the group consisting of: poly-L-lysine, poly-L-arginine, branched polyethylenimine (PEI), spermidine, spermine, chitosan [β-(1-4)-linked copolymer of 2-amino-2-deoxy-β-D-glucan (G1cN) and 2-acetamido-2-deoxy-β-D-glucan (G1cNAc)], Polyamine N7(CAS 29320-38-5) and Ethylenediaminomethyl polystyrene (CAS 177987-93-8).

3. The composition of claim 2, wherein said polycation is poly-L-lysine (PLL).

4. The composition of claim 3, wherein said poly-L-lysine is α-poly-L-lysine (α-PLL) or ε-poly-L-lysine (ε-PLL).

5. The composition of claim 4, wherein said poly-L-lysine is α-poly-L-lysine (α-PLL).

6. The composition of claim 1, wherein said composition is comprised of protein matrix particles having a mean particle size greater than 50 nm diameter.

7. The composition of claim 6, wherein said composition comprises protein matrix particles having a mean particle size diameter of 100 nm - 2000 nm.

8. The composition of claim 1 wherein the molar ratio of the combined one or more antigen to the combined one or more carrier protein is between 1 to 10 and 10 to 1.

9. The composition of claim 1 wherein the percentage of the combined one or more polycation by weight in the reaction mixture is 0.005 to 0.10%.

10. The composition of claim 1 comprising two or more antigens of interest.

11. The composition of claim 1, wherein said antigen of interest is a polysaccharide.

12. The composition of claim 11, wherein the polysaccharide is selected from the group consisting of a *Strepto-*

*coccus pneumoniae* polysaccharide, *Francisella tularensis* polysaccharide, *Bacillus anthracis* polysaccharide, *Haemophilus influenzae* polysaccharide, *Salmonella typhi* polysaccharide, *Citrobacter freundii* polysacchardie, *Salmonella* species polysaccharide, *Shigella* polysaccharide, or *Neisseria meningitidis* polysaccharide.

13. The composition of claim 12, wherein said *Streptococcus pneumoniae* polysaccharide is selected from the group consisting of capsular type 3, 4, 6B, 7A, 7B, 7C, 7F, 9A, 9L, 9N, 9V, 12A, 12B, 12F, 14, 15A, 15B, 15C, 15F, 17, 18B, 18C, 19F, 23F, 25A, 25F, 33F, 35, 37, 38, 44, or 46.

14. The composition of claim 1, wherein the one or more carrier protein is selected from the group consisting of diphtheria toxoid, CRM197, tetanus toxoid, *Pseudomonas aeruginosa* exotoxin A or a mutant thereof, cholera toxin B subunit, tetanus toxin fragment C, bacterial flagellin, pneumolysin, an outer membrane protein of *Neisseria meningitidis*, *Pseudomonas aeruginosa* Hcp1 protein, *Escherichia coli* heat labile enterotoxin, shiga-like toxin, human LTB protein, listeriolysin O, a protein extract from whole bacterial cells, the dominant negative inhibitor (DNI) mutant of the protective antigen of *Bacillus anthracis*, or *Escherichia coli* beta-galactosidase.

15. A method of making an immunogenic composition comprising (i) mixing an antigen of interest with a carrier protein and a polycation to form a mixture and (ii) cross-linking said carrier protein and polycation to form a carrier protein/polycation matrix entrapping said antigen of interest.

16. A method of eliciting an immune response in a mammal to an antigen of interest, said method comprising administering to said mammal an immunogenic composition according to claim 1.

17. The method of claim 16, wherein said mammal is a human.

18. A vaccine composition comprising two or more different immunogenic compositions according to claim 1.

19. A method of vaccinating a subject against an infectious agent that naturally bears an antigen of interest, said method comprising administering a composition according to claim 1, wherein at least one of said one or more antigen of interest in said immunogenic composition is said antigen of interest of said infectious agent, to a subject in an amount sufficient to elicit an immune response in the subject to said antigen of interest of said infectious agent.

* * * * *